(12) United States Patent
Saripalli et al.

(10) Patent No.: US 11,404,145 B2
(45) Date of Patent: Aug. 2, 2022

(54) MEDICAL MACHINE TIME-SERIES EVENT DATA PROCESSOR

(71) Applicant: GE Precision Healthcare LLC, Wauwatosa, WI (US)

(72) Inventors: Venkata Ratna Saripalli, San Ramon, CA (US); Gopal Avinash, San Ramon, CA (US); Min Zhang, San Ramon, CA (US); Ravi Soni, San Ramon, CA (US); Jiahui Guan, San Ramon, CA (US); Dibyajyoti Pati, San Ramon, CA (US); Zili Ma, San Ramon, CA (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 96 days.

(21) Appl. No.: 16/697,736

(22) Filed: Nov. 27, 2019

(65) Prior Publication Data

US 2020/0337648 A1    Oct. 29, 2020

Related U.S. Application Data

(60) Provisional application No. 62/838,022, filed on Apr. 24, 2019.

(51) Int. Cl.
*G06N 3/08* (2006.01)
*A61B 5/00* (2006.01)
(Continued)

(52) U.S. Cl.
CPC ........... *G16H 10/00* (2018.01); *A61B 5/7267* (2013.01); *G06F 9/451* (2018.02); *G06N 3/0445* (2013.01);
(Continued)

(58) Field of Classification Search
CPC .... A61B 5/7275; A61B 5/7267; G06N 20/20; G06N 3/0445; G06N 20/00; G06N 3/08;
(Continued)

(56) References Cited

U.S. PATENT DOCUMENTS

| 10,490,309 B1* | 11/2019 | McNair | .................. G16H 10/60 |
| 2005/0119534 A1* | 6/2005 | Trost | ...................... G16H 20/60 |
| | | | 600/300 |

(Continued)

FOREIGN PATENT DOCUMENTS

WO     2013036677     3/2013

OTHER PUBLICATIONS

"Devin Soni, Supervised vs. Unsupervised Learning, Mar. 22, 2018, towards data science, https://towardsdatascience.com/supervised-vs-unsupervised-learning-14f68e32ea8d" (Year: 2018).*

(Continued)

*Primary Examiner* — Joseph M Dietrich
*Assistant Examiner* — Michael T. Holtzclaw
(74) *Attorney, Agent, or Firm* — Hanley, Flight & Zimmerman, LLC

(57) ABSTRACT

Systems, apparatus, instructions, and methods for medical machine time-series event data processing are disclosed. An example time series event data processing apparatus includes memory storing instructions and one-dimensional time series healthcare-related data; and at least one processor. The example at least one processor is to: execute artificial intelligence model(s) trained on aggregated time series data to at least one of a) predict a future medical machine event, b) detect a medical machine event, or c) classify the medical machine event using the one-dimensional time series healthcare-related data; when the artificial intelligence model(s) are executed to predict the future medical machine event, output an alert related to the pre- (Continued)

dicted future medical machine event to trigger a next action; and when the artificial intelligence model(s) are executed to detect and/or classify the medical machine event, label the medical machine event and output the labeled event to trigger the next action.

20 Claims, 22 Drawing Sheets

(51) Int. Cl.
| | |
|---|---|
| G16H 10/00 | (2018.01) |
| G16H 50/30 | (2018.01) |
| G16H 40/67 | (2018.01) |
| G16H 10/60 | (2018.01) |
| G16H 15/00 | (2018.01) |
| G06F 9/451 | (2018.01) |
| G06N 20/00 | (2019.01) |
| G06N 20/20 | (2019.01) |
| G06N 3/04 | (2006.01) |

(52) U.S. Cl.
CPC .............. *G06N 3/08* (2013.01); *G06N 20/00* (2019.01); *G06N 20/20* (2019.01); *G16H 10/60* (2018.01); *G16H 15/00* (2018.01); *G16H 40/67* (2018.01); *G16H 50/30* (2018.01); *A61B 5/7275* (2013.01); *G06T 2207/20081* (2013.01); *G06T 2207/20084* (2013.01)

(58) Field of Classification Search
CPC .... G06N 3/0454; G06N 3/0472; G06N 3/088; G06N 3/084; G16H 10/60; G16H 15/00; G16H 50/30; G16H 40/67; G16H 50/20; G16H 50/70; G06F 9/451; G06T 2207/20081; G06T 2207/20084
See application file for complete search history.

(56) References Cited

U.S. PATENT DOCUMENTS

| | | | | |
|---|---|---|---|---|
| 2016/0135706 | A1* | 5/2016 | Sullivan | A61N 1/0484 600/301 |
| 2017/0032243 | A1* | 2/2017 | Corrado | G06N 3/04 |
| 2018/0107791 | A1* | 4/2018 | Guo | G06Q 40/08 |
| 2018/0315182 | A1* | 11/2018 | Rapaka | G16H 50/70 |
| 2019/0034591 | A1* | 1/2019 | Mossin | G16H 50/30 |
| 2019/0286990 | A1* | 9/2019 | Kenney | G06N 3/0454 |
| 2019/0362846 | A1* | 11/2019 | Vodencarevic | G16H 50/30 |
| 2019/0371475 | A1 | 12/2019 | Oliveira et al. | |
| 2019/0374160 | A1* | 12/2019 | Yin | A61B 5/486 |
| 2020/0185102 | A1* | 6/2020 | Leventhal | G06F 40/295 |
| 2020/0327456 | A1* | 10/2020 | Sathe | G06K 9/6231 |
| 2020/0327986 | A1* | 10/2020 | Kurniawan | G16H 50/70 |
| 2021/0056413 | A1* | 2/2021 | Cheung | G06N 3/08 |
| 2021/0076966 | A1* | 3/2021 | Grantcharov | A61B 5/364 |

OTHER PUBLICATIONS

"Kayla Ferguson, Why It's Important to Standardize Your Data, Dec. 10, 2018, humans of data, https://humansofdata.atlan.com/2018/12/data-standardization/" (Year: 2018).*
Anicka Slachta, "Deep learning ECG analysis facilitates screening for hyperkalemia,"Apr. 10, 2019, 4 pages.
Faust et al., "Deep learning for healthcare applications based on physiological signals: A review," Computer Methods and Programs in Biomedicine vol. 161, Jul. 2018, 13 pages.
Shoham et al., The AI Index 2018, Annual Report. In AI Index Steering Committee Human-Centered AI Initiative, Stanford, University, Stanford, CA, Dec. 2018, 94 pages.
Abadi et al., TensorFlow:Large-Scale Machine Learning on Heterogeneous Systems. https://www.tensorflow.org, Nov. 9, 2015, 19 pages.
Yangqing Jia et al., Caffe: Convolutional architecture for fast feature embedding. In Proceedings of the ACM International Conference on Multimedia, MM '14, Orlando, FL, USA, Nov. 3-7, 2014, 4 pages.
Tianqi Chen et al., MXNet: A Flexible and Efficient Machine Learning Library for Heterogeneous Distributed Systems. In Neural Information Processing Systems, Workshop on Machine Learning Systems, 2015, 6 pages.
Frank Seide et al., CNTK: Microsoft's Open-Source Deep-Learning Toolkit. In KDD. Association for Computing Machinery, 2016, 5 pages. Abstract only.
Adam Paszke et al.,Automatic Differentiation in PyTorch. In NIPS Autodiff Workshop, 2017, 4 pages.
Francois Chollet et al., Keras. https://keras.io, 2015, 5 pages.
Jeremy Howard et al.,. Fastai:. https://github.com/fastai/fastai, last retrieved on Apr. 27, 2020, 6 pages.
Piero Molino et al., Ludwig: a type-based declarative deep learning toolbox, 2019, 15 pages.
McInnes et al., UMAP: Uniform Manifold Approximation and Projection for Dimension Reduction. ArXiv e-prints, 2018, 51 pages.
Karen Simonyan et al., Deep Inside Convolutional Networks: Visualising Image Classification Models and Saliency Maps. In 2nd International Conference on Learning Representations, ICLR 2014, Banff, AB, Canada, Apr. 14-16, 2014, Workshop Track Proceedings, 8 pages.
Mukund Sundararajan et al., Axiomatic Attribution for Deep Networks. In Proceedings of the 34th International Conference on Machine Learning, ICML 2017, Sydney, NSW, Australia, Aug. 6-11, 2017, 11 pages.
Chris Olah et al., Feature Visualization, https: //distill.pub/2017/feature visualization, Nov. 7, 2017, 9 Pages.
Bee Lim et al., Enhanced Deep Residual Networks for Single Image Super-Resolution. In 2017 IEEE Conference on Computer Vision and Pattern Recognition Workshops, CVPR Workshops 2017, Honolulu, HI, USA, Jul. 21-26, 2017, 9 pages.
Tero Karras et al., Progressive Growing of GANs for Improved Quality, Stability, and Variation. In 6th International Conference on Learning Representations, ICLR 2018, Vancouver, BC, Canada, Apr. 30-May 3, 2018, Conference Track Proceedings, 26 pages.
Ian J. Goodfellow et al., Explaining and Harnessing Adversarial Examples. In 3rd International Conference on Learning Representations, ICLR 2015, San Diego, CA, USA, May 7-9, 2015, Conference Track Proceedings, 11 pages.
Alec Radford et al., Unsupervised Representation Learning with Deep Convolutional Generative Adversarial Networks. In 4th International Conference on Learning Representations, ICLR 2016, San Juan, Puerto Rico, May 2-4, 2016, Conference Track Proceedings, 16 pages.
Jun-Yan Zhu et al., Unpaired Image-to-Image Translation using Cycle Consistent Adversarial Networks. In 2017 IEEE International Conference on Computer Vision (ICCV), 10 pages.
Greg Brockman et al., OpenAI Gym, 2016, 4 pages.
Sutton et al., A. G. Introduction to reinforcement. Complete Draft Nov. 5, 2017, 445 pages.
Mahmud et al., Applications of Deep Learning and Reinforcement Learning to Biological Data, IEEE Trans. Neural Netw. Learn. Syst., 2018, doi: 10.1109/TNNLS.2018.2790388, 33 pages.
Topol, "High-performance medicine: the convergence of human and artificial intelligence", https://www.nature.com/articles/s41591-018-0300-7,last retrieved on Apr. 27, 2020, 13 pages.
Niranjani Prasad et al., A Reinforcement Learning Approach to Weaning of Mechanical Ventilation in Intensive Care Units, 2017, 10 pages.
Pablo Escandell-Montero et al., Optimization of anemia treatment in hemodialysis patients via reinforcement learning. Artificial Intelligence in Medicine, 62(1):47-60, 2014. ISSN 0933-3657, 17 pages.
Nemati et al., Optimal medication dosing from suboptimal clinical examples: A deep reinforcement learning approach. In 2016 38th

(56) References Cited

OTHER PUBLICATIONS

Annual International Conference of the IEEE Engineering in Medicine and Biology Society (EMBC), pp. 2978-2981, Aug. 2016, Abstract only.
Padmanabhan et al., Closed-loop control of anesthesia and mean arterial pressure using reinforcement learning. In 2014 IEEE Symposium on Adaptive Dynamic Programming and Reinforcement Learning (ADPRL), pp. 1-8, Dec. 2014, 11 pages.
Martina Mueller et al., Can machine learning methods predict extubation outcome in premature infants as well as clinicians? Journal of neonatal biology, 2013, 18 pages.
Hung-Ju Kuo et al., Improvement in the prediction of ventilator weaning outcomes by an artificial neural network in a medical icu. Respiratory care, 60(11): 1560-1569, 2015, 10 pages.
Yuanyuan Gao et al., Incorporating association rule networks in feature category-weighted naive bayes model to support weaning decision making. Decision Support Systems, 2017, Abstract only.
Hyung-Chul et al., Vital Recorder—a free research tool for automatic recording of high-resolution time-synchronised physiological data from multiple anaesthesia devices. Sci Rep. 2018, 8 pages.
Samudra et al., Scheduling operating rooms: achievements, challenges and pitfalls, 2016, 42 pages.
Li-Fang Cheng et al., Sparse Multi-Output Gaussian Processes for Medical Time Se-ries Prediction. ArXiv e-prints, Mar. 2017, 62 pages.
Brunton et al., "Extracting Spatial-Temporal Coherent Patterns in Large-Scale Neural Recordings Using Dynamic Mode Decomposition," Journal of Neuroscience Methods, vol. 258, Jan. 2016, Abstract only.
Joshua L Proctor et al., Dynamic mode decomposition with control. SIAM Journal on Applied Dynamical Systems, 15(1): 142-161, 2016, 20 pages.
Omer Gottesman et al., Evaluating reinforcement learning algorithms in observational health settings. CoRR,abs/1805.12298, 2018, 16 pages.
Lina Zhou et al., Machine learning on big data: Opportunities and challenges. Neurocomputing, 237:350-361, 2017, Abstract only.
Cao Xiao et al., Opportunities and challenges in developing deep learning models using electronic health records data: a systematic review. In JAMIA, 2018, 10 pages.
Marzyeh Ghassemi et al., Opportunities in machine learning for healthcare, 2018, 10 pages.
Andre Esteva et al., A guide to deep learning in healthcare. Nature medicine, 2019, 7 pages.
Xing Wang et al., A machine learning approach to false alarm detection for critical arrhythmia alarms. In 2015 IEEE 14th international conference on machine learning and applications (ICMLA), pp. 202-207. IEEE, 2015, Abstract only.
Patrick Schwab et al., Not to cry wolf: Distantly supervised multitask learning in critical care, 2018, 14 pages.
Richard S Sutton et al., Introduction to reinforcement learning, vol. 2. MIT press Cambridge, 1998, 352 pages.
Mnih Volodymyr et al., Human-level control through deep reinforcement learning, 2015, 13 pages.
Omid Sayadi et al., Life-threatening arrhythmia verification in icu patients using the joint cardiovascular dynamical model and a bayesian filter. IEEE Transactions on Biomedical Engineering, 2011, 10 pages.
Rebeca Salas-Boni et al., False ventricular tachycardia alarm suppression in the icu based on the discrete wavelet transform in the ecg signal. Journal of electrocardiology, 2014, Abstract only.
Joachim Behar et al., Ecg signal quality during arrhythmia and its application to false alarm reduction. IEEE transactions on biomedical engineering, 60 (6): 1660-1666, 2013, 8 pages.
Gari D Clifford et al., The physionet/computing in cardiology challenge 2015: reducing false arrhythmia alarms in the icu. In 2015 Computing in Cardiology Conference (CinC), pp. 273-276. IEEE, 2015, 8 pages.
Plesinger et al., Taming of the monitors: reducing false alarms in intensive care units. Physiological measurement, 2016, Abstract only.
Volodymyr et al., Asynchronous methods for deep reinforcement learning. In International conference on machine learning, pp. 1928-1937, 2016, 19 pages.
Leo Kobayashi et al., Development and deployment of an open, modular, near-real-time patient monitor datastream conduit toolkit to enable healthcare multimodal data fusion in a live emergency department setting for experimental bedside clinical informatics research. IEEE Sensors Letters, 3(1):1-4, 2018, Abstract only, 2 pages.
Acharya et al., "Deep convolutional neural network for the automated detection and diagnosis of seizure using EEG signals," Computers in Biology and Medicine 100 (2018) 270-278, 9 pages.
Johnson et al., "Machine Learning and Decision Support in Critical Care," Proceedings of the IEEE, vol. 104, No. 2, Feb. 2016, 23 pages.
Ge, "Hospital leverages Carestation Insights to reduce average fresh gas flow rates," 2017, 2 pages.
Baytas et al., "Patient Subtyping via Time-Aware LSTM Networks," 2017 research Paper, 10 pages.
Chul Lee et al., "Vital Recorder—a free research tool for automatic recording of high-resolution time-synchronised physiological data from multiple anaesthesia devices," 2018, 8 pages.
Benaich et al., "State of AI Report," Jun. 28, 2019, 136 pages.
Luo et al., "Multivariate Time Series Imputation with Generative Adversarial Networks," 32nd Conference on Neural Information Processing Systems (NeurIPS 2018), Montréal, Canada, 12 pages.
United States Patent and Trademark Office, "Final Office action," issued in connection with U.S. Appl. No. 16/656,034, dated Feb. 9, 2022, 31 pages.

\* cited by examiner

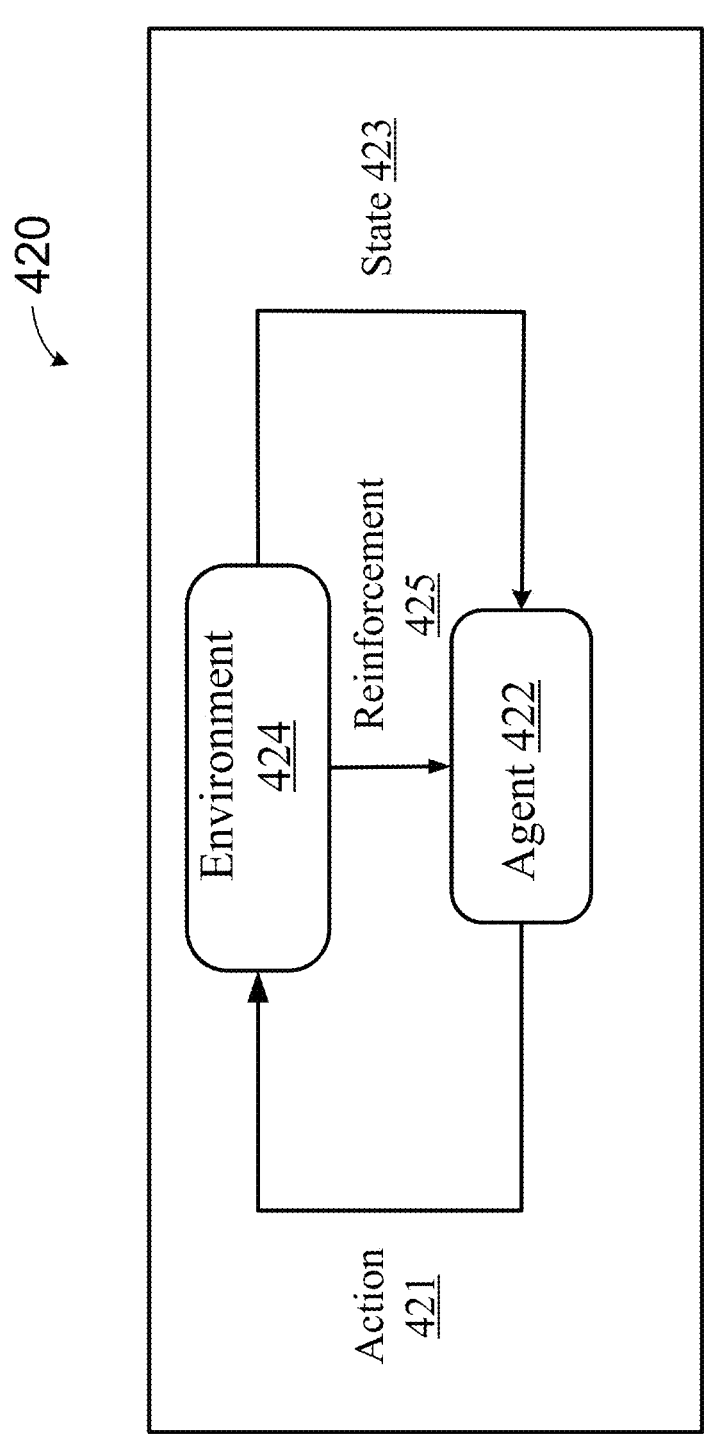

MEDICAL MACHINE TIME-SERIES EVENT DATA PROCESSOR

CROSS-REFERENCE TO RELATED APPLICATIONS

This patent arises from U.S. Provisional Patent Application Ser. No. 62/838,022, which was filed on Apr. 24, 2019. U.S. Provisional Patent Application Ser. No. 62/838,022 is hereby incorporated herein by reference in its entirety. Priority to U.S. Provisional Patent Application Ser. No. 62/838,022 is hereby claimed.

FIELD OF THE DISCLOSURE

This disclosure relates generally to medical data processing and, more particularly, to a medical machine time-series event data processor and associated methods.

BACKGROUND

The statements in this section merely provide background information related to the disclosure and may not constitute prior art.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored can include patient medication orders, medical histories, imaging data, test results, diagnosis information, management information, and/or scheduling information, for example. A wealth of information is available, but the information can be siloed in various separate systems requiring separate access, search, and retrieval. Correlations between healthcare data remain elusive due to technological limitations on the associated systems.

Further, healthcare data suffers from noise and lack of ground truth. Such data cannot effectively and reliably be leveraged until noise is removed and ground truth is established, particularly in healthcare where patient lives can be at risk. Existing solutions are deficient in addressing these and other related concerns.

BRIEF DESCRIPTION

Systems, apparatus, instructions, and methods for medical machine time-series event data processing are disclosed.

Certain examples provide a time series event data processing apparatus including memory storing instructions and one-dimensional time series healthcare-related data; and at least one processor. The example at least one processor is to: execute one or more artificial intelligence models trained on aggregated time series data to at least one of a) predict a future medical machine event, b) detect a medical machine event, or c) classify the medical machine event using the one-dimensional time series healthcare-related data; when the one or more artificial intelligence models are executed to predict the future medical machine event, output an alert related to the predicted future medical machine event to trigger a next action; when the one or more artificial intelligence models are executed to detect the medical machine event, label the medical machine event and output the labeled event to trigger the next action; and when the one or more artificial intelligence models are executed to classify the medical machine event, label the medical machine event and output the labeled event to trigger the next action.

Certain examples provide at least one tangible computer-readable storage medium including instructions that, when executed, cause at least one processor to at least: execute one or more artificial intelligence models trained on aggregated time series data to at least one of a) predict a future medical machine event, b) detect a medical machine event, or c) classify the medical machine event using the one-dimensional time series healthcare-related data; when the one or more artificial intelligence models are executed to predict the future medical machine event, output an alert related to the predicted future medical machine event to trigger a next action; when the one or more artificial intelligence models are executed to detect and classify the medical machine event, label the medical machine event and output the labeled event to trigger the next action; and, when the one or more artificial intelligence models are executed to classify the medical machine event, label the medical machine event and output the labeled event to trigger the next action.

Certain examples provide a computer-implemented method for medical machine time-series event data processing. The example method includes executing one or more artificial intelligence models trained on aggregated time series data to at least one of a) predict a future medical machine event, b) detect a medical machine event, or c) classify the medical machine event using the one-dimensional time series healthcare-related data. The example method includes, when the one or more artificial intelligence models are executed to predict the future medical machine event, outputting an alert related to the predicted future medical machine event to trigger a next action. The example method includes, when the one or more artificial intelligence models are executed to detect the medical machine event, labeling the medical machine event and outputting the labeled event to trigger the next action. The example method includes, when the one or more artificial intelligence models are executed to classify the medical machine event, label the medical machine event and output the labeled event to trigger the next action

BRIEF DESCRIPTION OF DRAWINGS

FIGS. 4A-4G depict example artificial intelligence models.

DETAILED DESCRIPTION OF CERTAIN EMBODIMENTS

Figure 1:
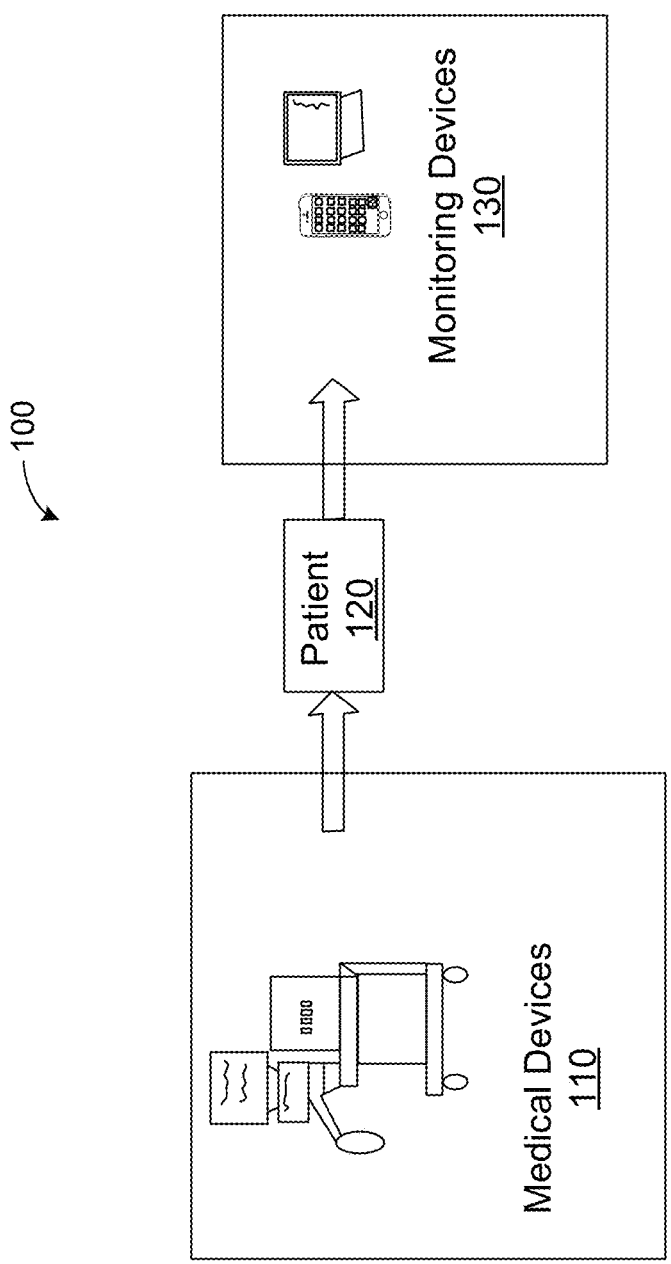
FIG. 1 is a block diagram of an example system including medical devices and associated monitoring devices for a patient.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

As used herein, singular references (e.g., "a", "an", "first", "second", etc.) do not exclude a plurality. The term "a" or "an" entity, as used herein, refers to one or more of that entity. The terms "a" (or "an"), "one or more", and "at least one" can be used interchangeably herein. Furthermore, although individually listed, a plurality of means, elements or method actions may be implemented by, e.g., a single unit or processor. Additionally, although individual features may be included in different examples or claims, these may possibly be combined, and the inclusion in different examples or claims does not imply that a combination of features is not feasible and/or advantageous.

The term "and/or" when used, for example, in a form such as A, B, and/or C refers to any combination or subset of A, B, C such as (1) A alone, (2) B alone, (3) C alone, (4) A with B, (5) A with C, (6) B with C, and (7) A with B and with C. As used herein in the context of describing structures, components, items, objects, and/or things, the phrase "at least one of A and B" is intended to refer to implementations including any of (1) at least one A, (2) at least one B, and (3) at least one A and at least one B. Similarly, as used herein in the context of describing structures, components, items, objects and/or things, the phrase "at least one of A or B" is intended to refer to implementations including any of (1) at least one A, (2) at least one B, and (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, and (3) at least one A and at least one B. Similarly, as used herein in the context of describing the performance or execution of processes, instructions, actions, activities, and/or steps, the phrase "at least one of A or B" is intended to refer to implementations including any of (1) at least one A, (2) at least one B, and (3) at least one A and at least one B.

In addition, it should be understood that references to "one embodiment" or "an embodiment" of the present disclosure are not intended to be interpreted as excluding the existence of additional embodiments that also incorporate the recited features.

Medical data can be obtained from imaging devices, sensors, laboratory tests, and/or other data sources. Alone or in combination, medical data can assist in diagnosing a patient, treating a patient, forming a profile for a patient population, influencing a clinical protocol, etc. However, to be useful, medical data must be organized properly for analysis and correlation beyond a human's ability to track and reason. Computers and associated software and data constructs can be implemented to transform disparate medical data into actionable results.

For example, imaging devices (e.g., gamma camera, positron emission tomography (PET) scanner, computed tomography (CT) scanner, X-Ray machine, magnetic resonance (MR) imaging machine, ultrasound scanner, etc.) generate two-dimensional (2D) and/or three-dimensional (3D) medical images (e.g., native Digital Imaging and Communications in Medicine (DICOM) images) representative of the parts of the body (e.g., organs, tissues, etc.) to diagnose and/or treat diseases. Other devices such as electrocardiogram (ECG) systems, echoencephalograph (EEG), pulse oximetry (SpO2) sensors, blood pressure measuring cuffs, etc., provide one-dimensional waveform and/or time series data regarding a patient.

The healthcare domain has seen a dramatic shift in machine learning and computational methods with the rise of deep learning and medical data availability. Data is the fundamental currency for solving many healthcare problems using computational methods. While volumes of medical data are becoming increasingly available, such big data has its own unique challenges. Medical data suffers from data privacy, sparsity, noise, quality, missing data, heterogeneity, and ground truth availability. Deep learning methods compared with traditional machine learning are scalable and efficient in learning the data patterns when provided with sufficient data. Medical devices such as anesthesia machines, ventilators, and monitoring systems are a rich source of data which help in processing, identifying, and alerting events that in turn serve as the basis for optimal/improved decision making. Alarm fatigue is an issue in medical alarms that is caused by the threshold-based alarm classification approach that is used in medical monitoring systems. To build smart alarm systems and use AI algorithms in practice, the problem of false alarms must be addressed, which involves a significant volume of correctly annotated data. It is expensive, time-consuming, and requires domain expertise to get trustworthy annotations of medical monitoring data.

Acquisition, processing, analysis, and storage of time-series data (e.g., one-dimensional waveform data, etc.) obtained from one or more medical machines and/or devices play an important role in diagnosis and treatment of patients in a healthcare environment. Devices involved in the workflow can be configured, monitored, and updated throughout operation of the medical workflow. Machine learning can be used to help configure, monitor, and update the medical workflow and devices.

Machine learning techniques, whether deep learning networks or other experiential/observational learning system, can be used to characterize and otherwise interpret, extrapolate, conclude, and/or complete acquired medical data from a patient, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

To be accurate and robust, machine learning networks must be trained and tested using data that is representative of data that will be processed by the deployed network model. Data that is irrelevant, inaccurate, and/or incomplete can result in a deep learning network model that provides an incorrect output in response to data input. Certain examples provide top-down systems and associated methods to capture and organize data (e.g., group, arrange with respect to an event, etc.), remove outliers, and/or otherwise align data with respect to a clinical event, trigger, other occurrence, etc., to form a ground truth for training, testing, etc., of a learning network model.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network (DLN), also referred to as a deep neural network (DNN), can be a training network (e.g., a training network model or device) that learns patterns based on a plurality of inputs and outputs. A deep learning network/deep neural network can be a deployed network (e.g., a deployed network model or device) that is generated from the training network and provides an output in response to an input.

The term "supervised learning" is a deep learning training method in which the machine is provided already classified data from human sources. The term "unsupervised learning" is a deep learning training method in which the machine is not given already classified data but makes the machine useful for abnormality detection. The term "semi-supervised learning" is a deep learning training method in which the machine is provided a small amount of classified data from human sources compared to a larger amount of unclassified data available to the machine.

The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data in a series of stages, examining the data for learned features.

The term "transfer learning" is a process of a machine storing the information used in properly or improperly solving one problem to solve another problem of the same or similar nature as the first. Transfer learning may also be known as "inductive learning". Transfer learning can make use of data from previous tasks, for example.

The term "active learning" is a process of machine learning in which the machine selects a set of examples for which to receive training data, rather than passively receiving examples chosen by an external entity. For example, as a machine learns, the machine can be allowed to select examples that the machine determines will be most helpful for learning, rather than relying only an external human expert or external system to identify and provide examples.

The term "computer aided detection" or "computer aided diagnosis" refer to computers that analyze medical data to suggest a possible diagnosis.

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines can utilize transfer learning when interacting with physicians to counteract the small dataset available in the supervised training. These deep learning machines can improve their computer aided diagnosis over time through training and transfer learning. However, a larger dataset results in a more accurate, more robust deployed deep neural network model that can be applied to transform disparate medical data into actionable results (e.g., system configuration/settings, computer-aided diagnosis results, image enhancement, etc.).

Certain examples provide a framework including a) a computer executing one or more deep learning (DL) models and hybrid deep reinforcement learning (RL) models trained on aggregated machine timeseries data converted into the single standardized data structure format and in an ordered arrangement per patient to predict one or more future events and summarize pertinent past machine events related to the predicted one or more future machine events on a consistent input time series data of a patient having the standardized data structure format; and b) a healthcare provider-facing interface of an electronic device for use by a healthcare provider treating the patient configured to display the predicted one or more future machine events and the pertinent past machine events of the patient.

In certain examples, machine signals, patient physiological signals, and a combination of machine and patient physiological signals provide improved prediction, detection, and/or classification of events during a medical procedure. The three data contexts are represented in Table 1 below, associated with example artificial intelligence models that can provide a prediction, detection, and/or classification using the respective data source. Data-driven predictions of events related to a medical treatment/procedure help to lower healthcare costs and improve the quality of care. Certain examples involve DL models, hybrid RL models, and DL+Hybrid RL combination models for prediction of such events. Similarly, data-driven detection and classification of events related to a patient and/or machine helps to lower healthcare costs and improve the quality of care. Certain examples involve DL models, hybrid RL models, and DL+Hybrid RL combination models for detection and classification of such events.

As shown below, machine data, patient monitoring data, and a combination of machine and monitoring data can be used with one or more artificial intelligence constructs to form one or more predictions, detections, and/or classifications, for example.

TABLE 1

Data source and associated prediction, detection, and/or classification model examples.

| Data Source | Prediction/Detection/Classification |
| --- | --- |
| Machine Data | DL |
|  | Hybrid RL |
|  | DL + Hybrid RL |
| Monitoring (Patient data) | DL |
|  | Hybrid RL |
|  | DL + Hybrid RL |
| Machine + Monitoring Data | DL |
|  | Hybrid RL |
|  | DL + Hybrid RL |

Certain examples deploy learned models in a live system for patient monitoring. Training data is to match collected data, so if live data is being collected during surgery, for example, the model is to be trained on live surgical data also. Training parameters can be mapped to deployed parameters for live, dynamic delivery to a patient scenario (e.g., in the operating room, emergency room, etc.). Also, one-dimensional (1D) time series event data (e.g., ECG, EEG, O2, etc.) is processed differently by a model than a 2D or 3D image. 1D time series event data can be aggregated and processed, for example.

Thus, as shown below, one or more medical devices can be applied to extract time-series data with respect to a patient, and one or more monitoring devices can capture and process such data. Benefits to one-dimensional, time-series data modeling include identification of more data-driven events to avoid false alarms (e.g., avoiding false alarm fatigue, etc.), provide quality event detection, etc. Other benefits include improved patient outcomes. Cost-savings can also be realized, such as reducing cost to better predict events such as when to reduce gas, when to take a patient off an oxygen ventilator, when to transfer a patient from operating room (OR) to other care, etc.

Other identification methods are threshold based rather than personalized. Certain examples provide personalized modeling, based on a patient's own vitals, machine data from a healthcare procedure, etc. For example, for patient heart rate, a smaller person has a different rate than heavier built person. As such, alarms can differ based on the person rather than conforming to set global thresholds. A model, such as a DL model, etc., can determine or predict when to react to an alarm versus turn the alarm off, etc. Certain examples can drive behavior, configuration, etc., of another machine (e.g., based on physiological conditions, a machine can send a notification to another machine to lower anesthesia, reduce ventilator, etc.; detect ventilator dystrophy and react to it, etc.).

As shown in an example system 100 of FIG. 1, one or more medical devices 110 (e.g., ventilator, anesthesia machine, intravenous (IV) infusion drip, etc.) administer to a patient 120, while one or more monitoring devices 130 (e.g., electrocardiogram (ECG) sensor, blood pressure sensor, respiratory monitor, etc.) gather data regarding patient vitals, patient activity, medical device operation, etc. Such data can be used to train an AI model, can be processed by a trained AI model, etc.

Figure 2:
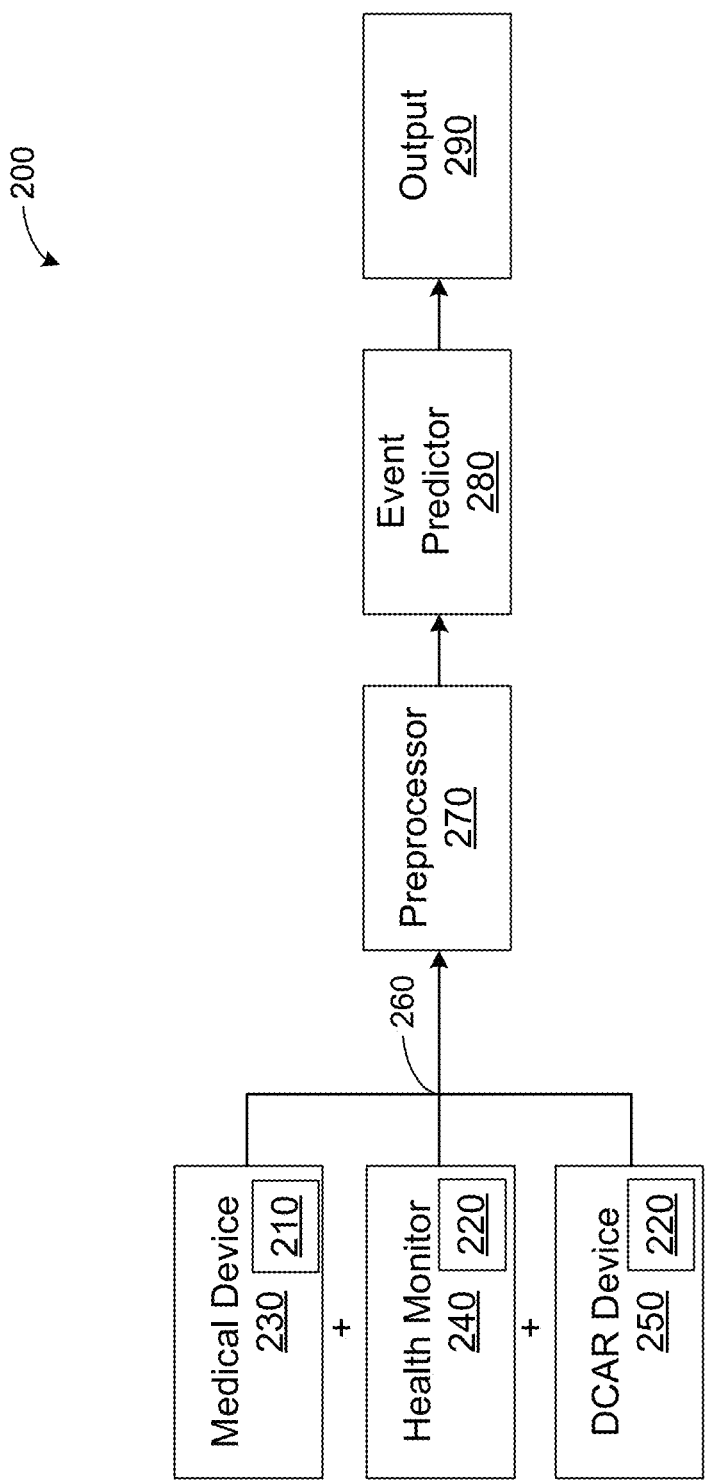
FIG. 2 is a block diagram of an example system to process machine and physiological data and apply one or more machine learning models to predict future events from the data.

Certain examples provide systems and methods for deep learning and hybrid reinforcement learning-based event prediction, detection, and/or classification. For example, as shown in an example system 200 of FIG. 2, machine data 210 and physiological (e.g., vitals, etc.) data 220 from one or more medical devices 230, mobile digital health monitors 240, one or more diagnostic cardiology (DCAR) devices 250, etc., is provided in a data stream 260 (e.g., continuous streaming, live streaming, periodic streaming, etc.) to a preprocessor 270 to pre-process the data and apply one or more machine learning models to detect events in the data stream 260, for example. The pre-processed data is provided from the preprocessor 270 to an event predictor 280, which applies one or more AI models, such as a DL model, a hybrid RL model, a DL+hybrid RL model, etc., to predict future events from the preprocessed data. The event predictor 280 forms an output 290 including one or more insights, alerts, actions, etc., for a system, machine, user, etc. For example, the event predictor 280 can predict, based on model(s) applied to the streaming 1D data, occurrence of event(s) such as heart attack, stroke, high blood pressure, accelerated heart rate, etc., and an actionable alert can be provided by the output 290 to adjust an IV drip, activate a sensor and/or other monitor, change a medication dosage, obtain an image, send data to another machine to adjust its settings/configuration, etc.

Figure 3:
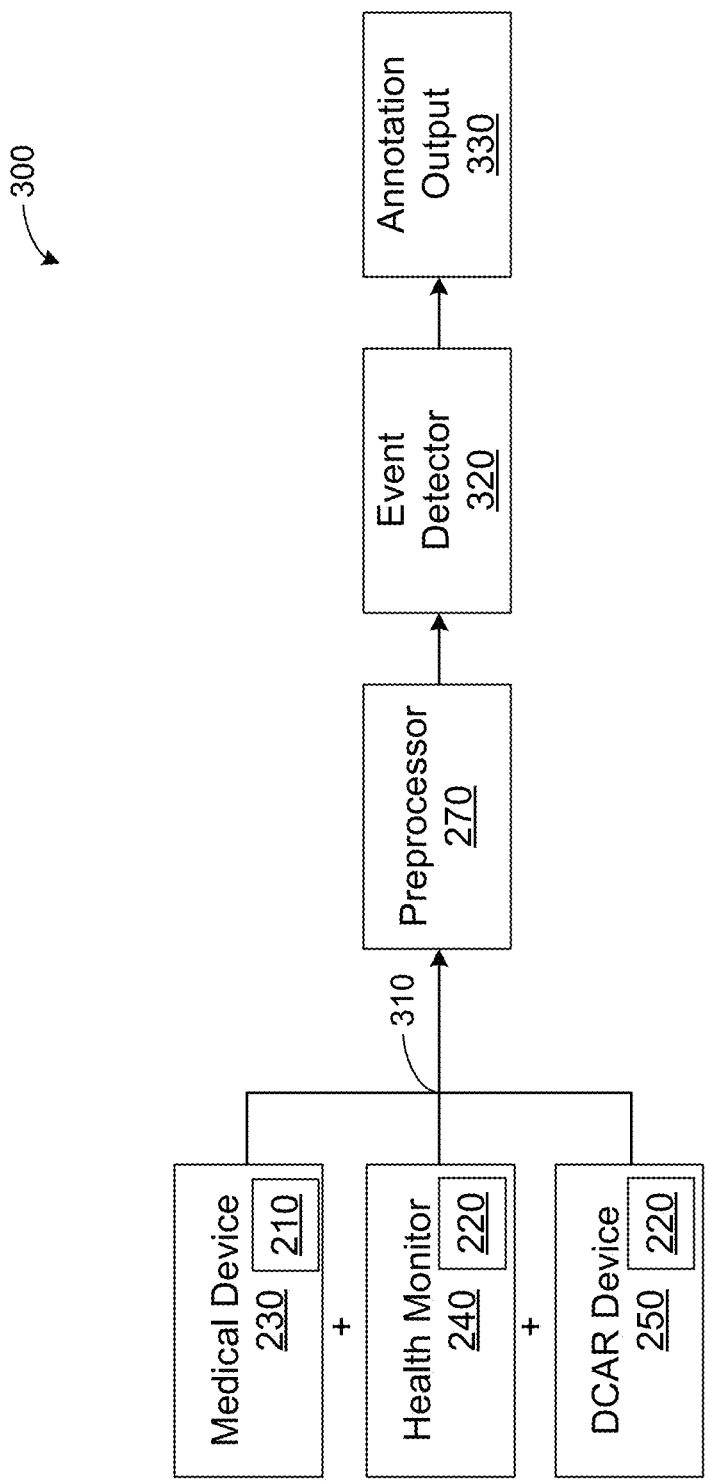
FIG. 3 is a block diagram of an example system to process machine and physiological data and apply one or more machine learning models to detect events that have occurred.

In certain examples, detection and event classification can also be facilitated using deep learning and hybrid reinforcement learning. FIG. 3 illustrates an example system 300 in which the machine data 210 and the physiological (e.g., vitals, etc.) data 220 from the one or more medical devices 230, mobile digital health monitors 240, one or more diagnostic cardiology (DCAR) devices 250, etc., is provided offline 310 (e.g., once a study and/or other exam has been completed, periodically at a certain time/interval or based on a current size of data collection, etc.) to the preprocessor 270 to pre-process the data and apply one or more machine learning models to detect events in the data set 310, for example. The pre-processed data is provided from the preprocessor 270 to an event detector 320, which applies one or more AI models, such as a DL model, a hybrid RL model, a DL+hybrid RL model, etc., to detect and classify events from the preprocessed data. The event detector 320 forms an annotation output 330 including labeled events, etc. For example, the event detector 320 can detect and classify, based on model(s) applied to the streaming 1D data, occurrence of event(s) such as heart attack, stroke, high blood pressure, accelerated heart rate, etc., and the event(s) can then be labeled to be used as ground truth 330 for training of an AI model, verification by a healthcare professional, adjustment of machine settings/configuration, etc.

Example Artificial Intelligence Network Models

In certain examples, a convolution neural network (CNN) and recurrent neural network (RNN) can be used alone or in combination to process data and extract event prediction. Other machine learning/deep learning/other artificial intelligence networks can be used alone or in combination.

Figure 4A:
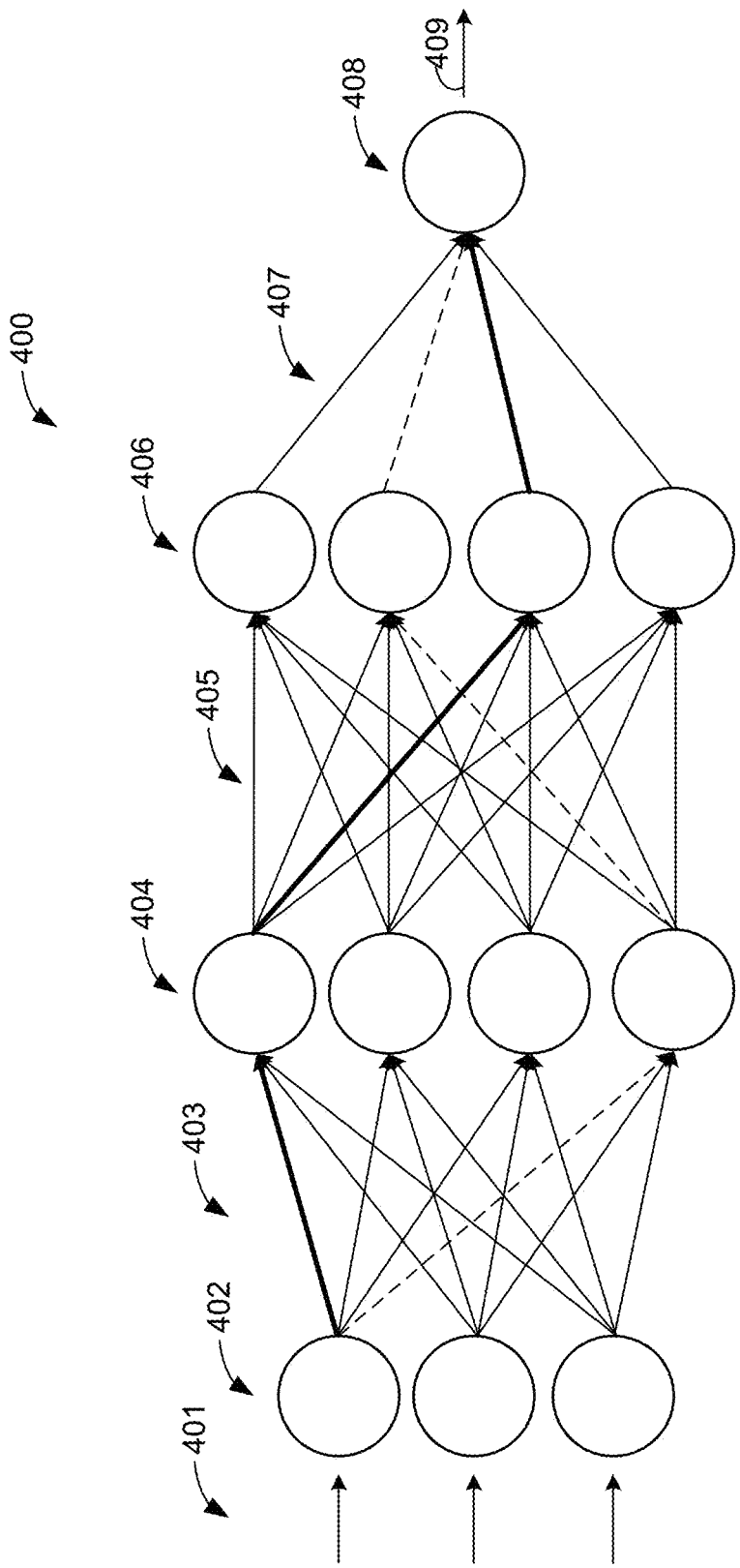

Convolutional neural networks are deep artificial neural networks that are used to classify images (e.g., associate a name or label with what object(s) are identified in the image, etc.), cluster images by similarity (e.g., photo search, etc.), and/or perform object recognition within scenes, for example. CNNs can be used to instantiate algorithms that can identify faces, individuals, street signs, tumors, platypuses, and/or many other aspects of visual data, for example. FIG. 4A illustrates an example CNN 400 including layers 402, 404, 406, and 408. The layers 402 and 404 are connected with neural connections 403. The layers 404 and 406 are connected with neural connections 405. The layers 406 and 408 are connected with neural connections 407. Data flows forward via inputs 401 from the input layer 402 to the output layer 408 and to an output 409.

The layer 402 is an input layer that, in the example of FIG. 4A, includes a plurality of nodes. The layers 404 and 406 are hidden layers and include, the example of FIG. 4A, a plurality of nodes. The neural network 400 may include more or less hidden layers 404, 406 than shown. The layer 408 is an output layer and includes, in the example of FIG. 4A, a node with an output 409. Each input 401 corresponds to a node of the input layer 402, and each node of the input layer 402 has a connection 403 to each node of the hidden layer 404. Each node of the hidden layer 404 has a connection 405 to each node of the hidden layer 406. Each node of the hidden layer 406 has a connection 407 to the output layer 408. The output layer 408 has an output 409 to provide an output from the example neural network 400.

Of connections 403, 405, and 407 certain example connections may be given added weight while other example connections may be given less weight in the neural network 400. Input nodes are activated through receipt of input data via inputs, for example. Nodes of hidden layers 404 and 406 are activated through the forward flow of data through the network 400 via the connections 403 and 405, respectively. The node of the output layer 408 is activated after data processed in hidden layers 404 and 406 is sent via connections 407. When the output node of the output layer 408 is activated, the node outputs an appropriate value based on processing accomplished in hidden layers 404 and 406 of the neural network 400.

Figure 4B:
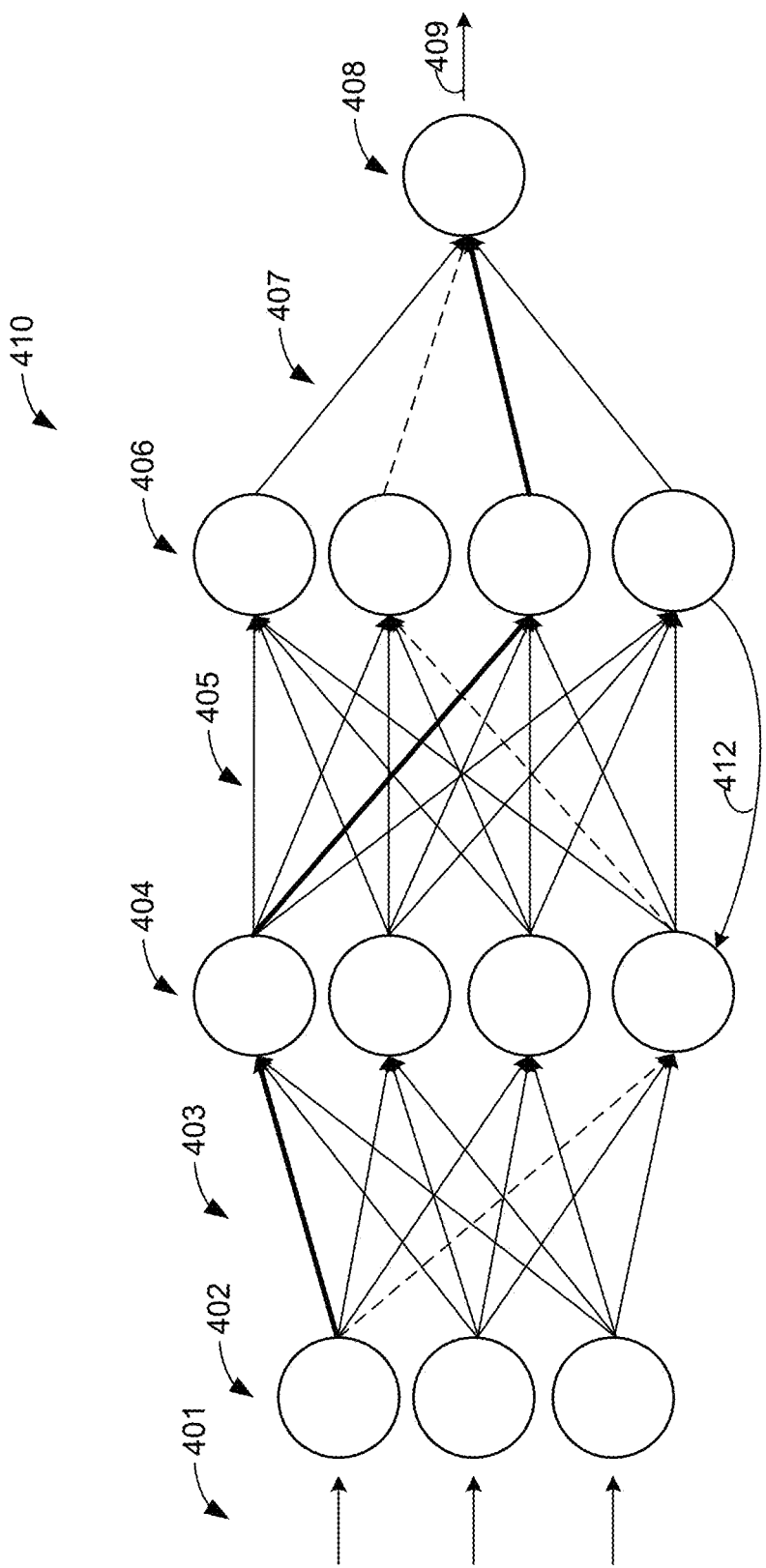

Recurrent networks are a powerful set of artificial neural network algorithms especially useful for processing sequential data such as sound, time series (e.g., sensor) data or written natural language, etc. A recurrent neural network can be implemented similar to a CNN but including one or more connections 412 back to a prior layer, such as shown in the example RNN 410 of FIG. 4B.

A reinforcement learning (RL) model is an artificial intelligence model in which an agent takes an action in an environment to maximize a cumulative award. RL is a computational approach to learning from interactions that is goal-focused, for example. RL can be model-free, in which no assumptions are made regarding the environment or data samples to learn a policy. Such approaches can be flexible to learn complex policies but can require many trials and training time for convergence.

FIG. 4C depicts an example RL network 420 in which an agent 422 operates with respect to an environment 424. An action 421 of the agent 422 results in a change in a state 423 of the environment 424. Reinforcement 425 is provided to the agent 422 from the environment 424 to provide a reward and/or other feedback to the agent 422. The state 423 and reinforcement 425 are incorporated into the agent 422 and influence its next action, for example.

Hybrid Reinforcement Models include a Deep Hybrid RL, for example. Reinforcement learning refers to goal-oriented algorithms, which learn how to attain a complex objective (goal) and/or maximize along a particular dimension over many steps/actions. For example, an objective can include to maximize points won in a game over many moves. Reinforcement learning models can start from a blank slate, and, under the right conditions, the model can achieve superior performance. Like a child incentivized by spankings and candy, these algorithms are penalized when they make the wrong decisions and rewarded when they make the right decisions to provide reinforcement. A hybrid deep reinforcement network can be configured as shown in the example 430 of FIG. 4D.

Figure 4D:
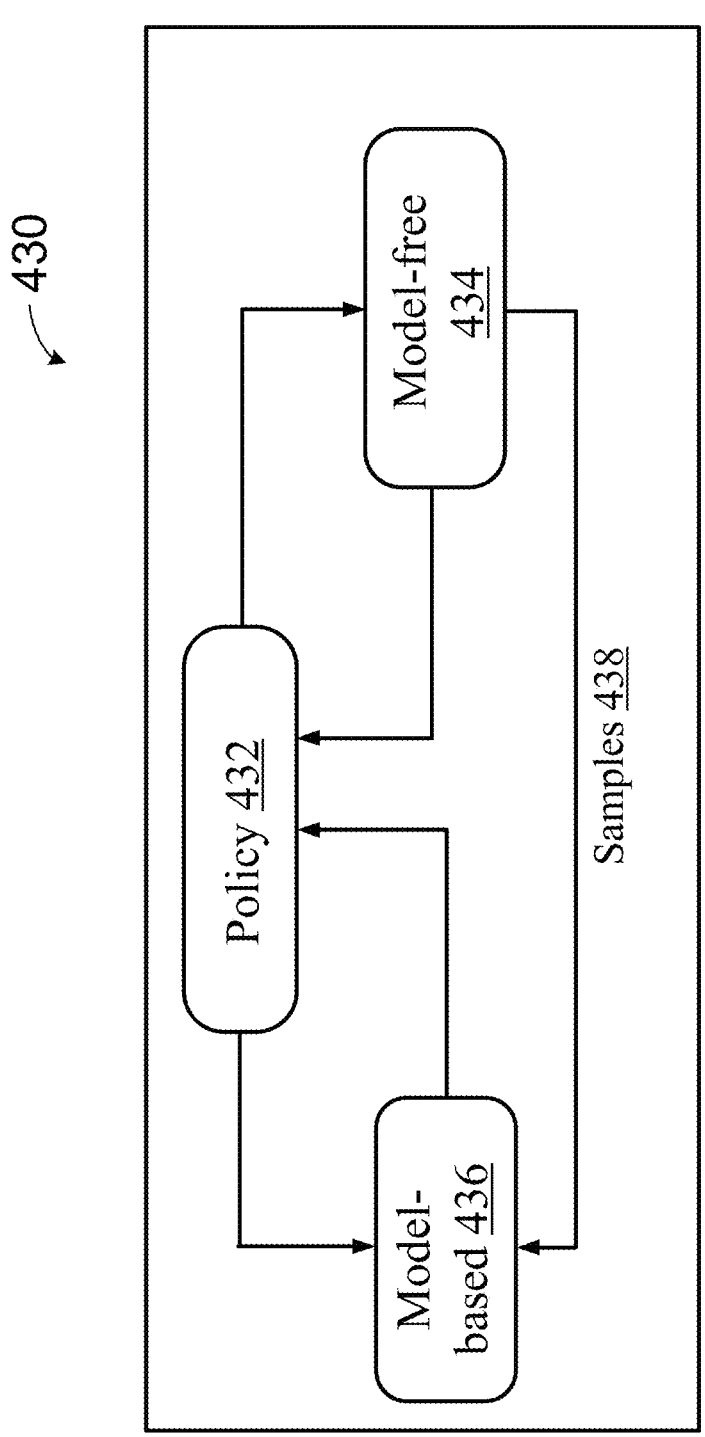

As shown in the example 430 of FIG. 4D, a policy 432 drives model-free deep reinforcement learning algorithm(s) 434 to learn tasks associated with processing of data, such as 1D waveform data, etc. Results of the model-free RL algorithm(s) 434 provide feedback to the policy 432 and generate samples 438 for model-based reinforcement algorithm(s) 436. The model-based RL algorithm(s) 430 operates according to the policy 432 and provides feedback to the policy 432 based on samples from the model-free RL algorithm(s) 434. Model-based RL algorithm(s) 436 are more sample-efficient and more flexible than task-specific policy(-ies) 432 learned with model-free RL algorithm(s) 434, for example. However, asymptotic performance of model-based RL algorithm(s) 436 is usually worse than model-free RL algorithm(s) 434 due to model bias, for example. For example, model-free RL algorithm(s) 434 are not limited by model accuracy and can therefore achieve better final performance, although at the expense of higher sample complexity. The hybrid deep RL models combined model-based 436 and model-free 434 RL algorithms (e.g., model-based algorithm(s) 436 to enable supervised initialization of policy 432 that can be fine-tuned with the model-free algorithm(s) 434, etc.) to accelerate model-free learning and improved sample efficiency, for example.

Certain examples apply hybrid RL models to facilitate determination and control of input and provide an ability to separate and/or combine information including ECG, spO2, blood pressure, other parameters. Early warning signs of a condition or health issue can be determined and used to alert a patient, clinician, other system, etc. A normal/baseline value can be determined, and deviation from the baseline (e.g., during the course of a surgical operation, etc.) can be determined. Signs of distress can be identified/predicted before an issue becomes critical. In certain examples, a look-up table can be provided to select one or more artificial intelligence networks based on particular available input and desired output. The lookup table can enable rule-based neural network selection to generate appropriate model(s), for example.

Other neural networks include transformer networks, graph neural networks, etc. A transformer or transformer network is a neural network architecture that transforms an input sequence to an output sequence using sequence transduction or neural machine translation (e.g., to process speech recognition, text-to-speech transformation, etc.), for example. The transformer network has memory to remember or otherwise maintain dependencies and connections (e.g., between sounds and words, etc.). For example, the transformer network can include a CNN with one or more attention models to improve speed of translation/transformation. The transformer can be implemented using a series of encoders and decoders (e.g., implemented using a neural network such as a feed forward neural network, CNN, etc., and one or more attention models, etc.). As such, the transformer network transforms one sequence into another sequence using the encoder(s) and decoder(s).

In certain examples, a transformer is applied to sequence and time series data. Compared with an RNN and/or long short-term memory (LSTM) model, the transformer has the following advantages. The transformer applies a self-attention mechanism that directly models relationships between all words in a sentence, regardless of their respective position. The transformer allows for significantly more parallelization. The transformer proposes to encode each position and applying the attention mechanism to relate two distant words of both the inputs and outputs with respect to itself, which then can be parallelized to accelerate training, for example. Thus, the transformer requires less computation to train and is a much better fit for modern machine learning hardware, speeding up training by up to an order of magnitude, for example.

Figure 4E:
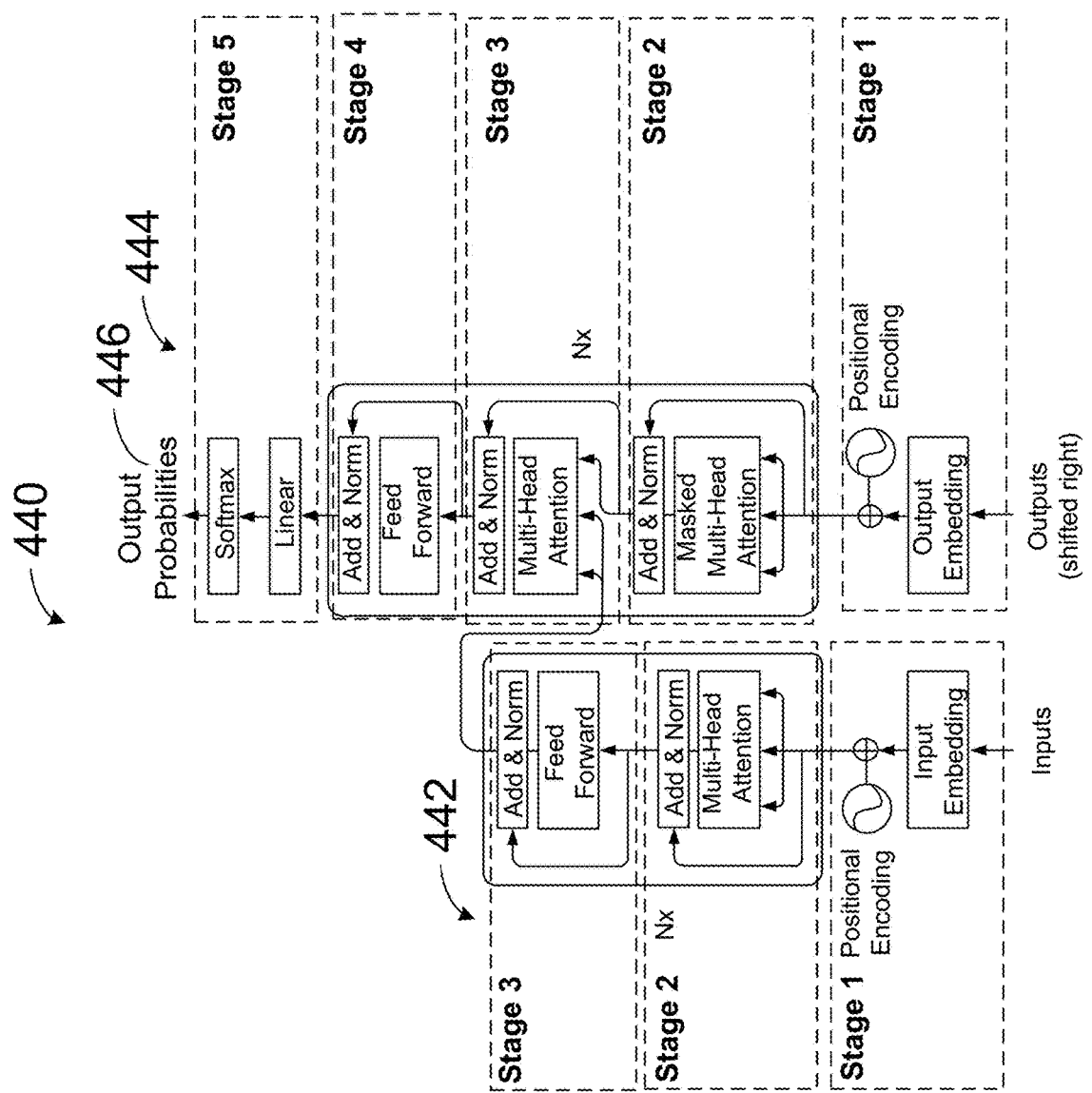

FIG. 4E shows an example transformer neural network 440 including three input stages and five output stages to transform an input sequence into an output sequence. The example transformer 440 includes an encoder 442 and a decoder 444. The encoder 442 processes input, and the decoder 444 generates output probabilities, for example. The encoder 442 includes three stages, and the decoder 444 includes five stages. Encoder 442 stage 1 represents an input as a sequence of positional encodings added to embedded inputs. Encoder 442 stages 2 and 3 include N layers (e.g., N=6, etc.) in which each layer includes a position-wise feedforward neural network (FNN) and an attention-based sublayer. Each attention-based sublayer of encoder 442 stage 2 includes four linear projections and multi-head attention logic to be added and normalized to be provided to the position-wise FNN of encoder 442 stage 3. Encoder 442 stages 2 and 3 employ a residual connection followed by a normalization layer at their output.

The example decoder 444 processes an output embedding as its input with the output embedding shifted right by one position to help ensure that a prediction for position i is dependent on positions previous to/less than i. In stage 2 of the decoder 444, masked multi-head attention is modified to prevent positions to attend to subsequent positions. Stages 3-4 of the decoder 444 include N layers (e.g., N=6, etc.) in which each layer includes a position-wise FNN and two attention-based sublayers. Each attention-based sublayer of decoder 444 stage 3 includes four linear projections and multi-head attention logic to be added and normalized to be provided to the position-wise FNN of decoder 444 stage 4. Decoder 444 stages 2-4 employ a residual connection followed by a normalization layer at their output. Decoder 444 stage 5 provides a linear transformation followed by a softmax function to normalize a resulting vector of K numbers into a probability distribution 446 including K probabilities proportional to exponentials of the K input numbers.

A graph neural network (GNN) is a neural network that operates on a graph structure. In a graph, vertices or nodes are connected by edges, which can be directed or undirected edges, for example. The GNN can be used to classify nodes in the graph structure, for example. For example, each node in the graph can be associated with a label, and node labels can be predicted by the GNN without ground truth. Given a partially labeled graph, for example, labels for unlabeled nodes can be predicted.

Figure 4F:
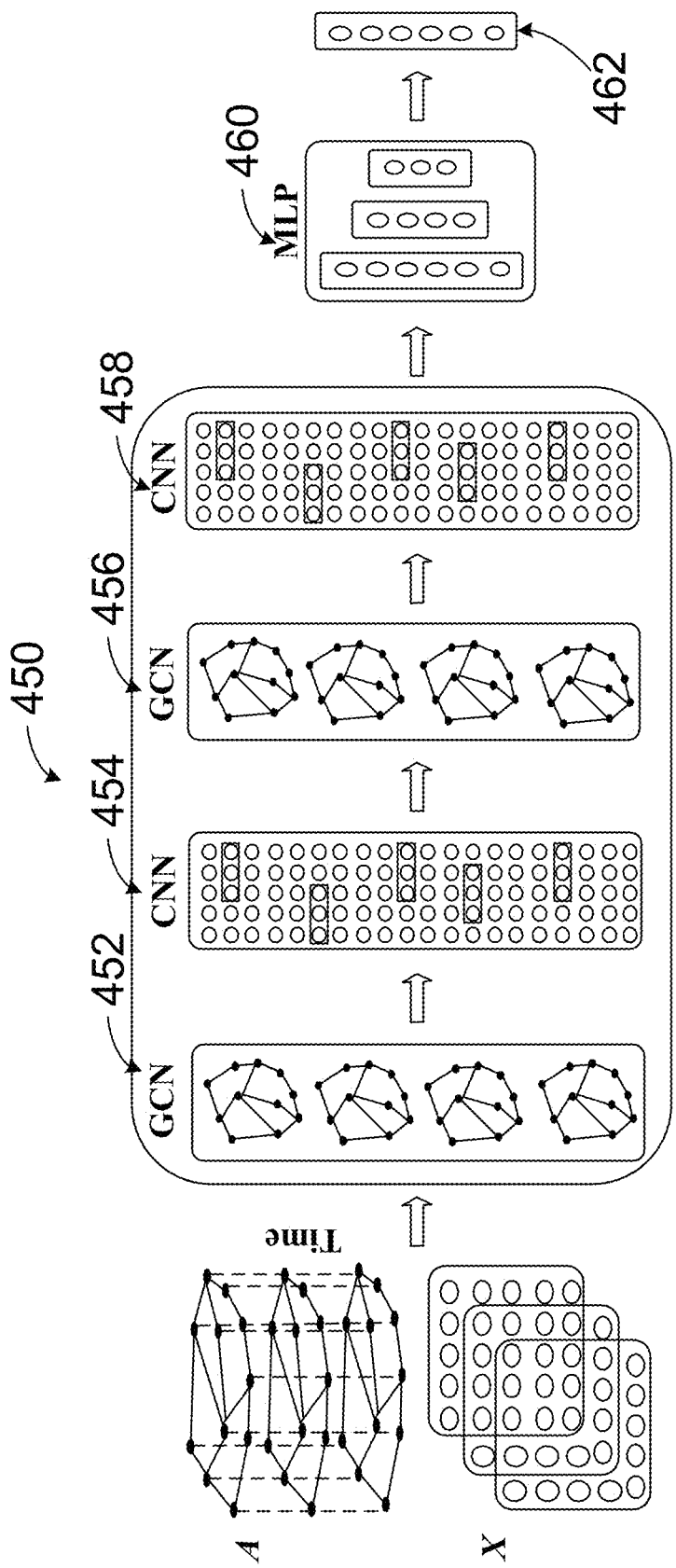

FIG. 4F shows an example GNN 450 in which a graph A includes a plurality of nodes and edges, wherein each node is associated with a medical machine/device and linked with a sparse feature matrix $X_i$ with time-series monitoring data at time i. Machine events $y_i$ are stages/classes that the network 450 is trying to detect/predict/classify during the time i. As shown in the example of FIG. 4F, the graph A and matrix X are provided as input to the GNN 450 including a first graph convolutional network (GCN) layer 452 that operates on A and X to determine spatial dependency followed by a CNN 454 that processes X over time to determine temporal dependency. The GCN-CNN layer pair 452, 454 is followed by another GCN 456 and CNN 458 which produces a multilayer perceptron network 460, which is a feedforward neural network that provides a linear activation function to map weighted inputs to an output set y 462 representing predicted machine events at a future time i.

Figure 4G:
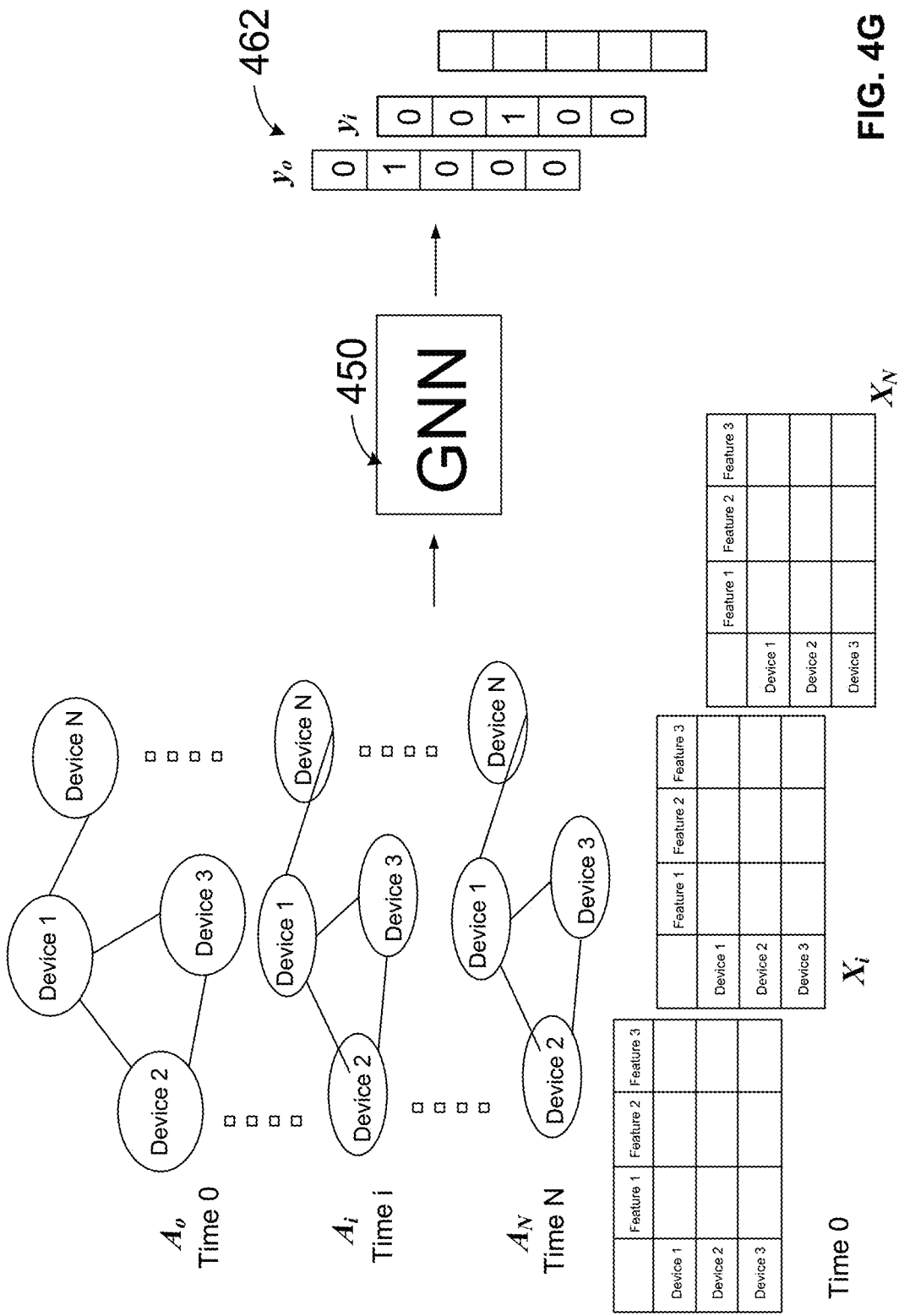

FIG. 4G shows an example view of the GNN 450 including a plurality of medical machines/devices 1-N at a plurality of points in time 0-N forming the graph A. Each machine/device 1-N can be associated with one or more features 1-N organized in matrix X at times 0-N, forming matrices $X_{0-N}$. The graph $A_{0-N}$ and matrices $X_{0-N}$ are provided to the GNN 450 to produce a predicted set of machine events y 462 occurring a times 0, 1, ... N.

Thus, for example, the GNN 450, including one or more GCNs 452, 456 and one or more CNNs 454, 458, etc., can be used to process signal data such as EEG, ECG, breathing, SpO2, etc., and correlate patient physiological signals to classify the signals, detect event(s) occurring with respect to the signals, predict occurrence of an event based on the modeled signals, etc.

Example Deep Learning Processing of One-Dimensional Signal Data for Detection, Classification, and Prediction of Medical Events Certain examples include aggregation techniques for detection, classification, and prediction of medical events based on DL processing of time series data. Different signals can be obtained, and different patterns can be identified for different circumstances. From a large aggregated data set, a subset can be identified and processed as relevant for a particular "-ology" or circumstance. Data can be partitioned into a relevant subset. For example, four different hospitals are collecting data, and the data is then partitioned to focus on cardiac data, etc. Partitioning can involve clustering, etc. Metadata can be leveraged, and data can be cleaned to reduce noise, artifacts, outliers, etc. Missing data can be interpolated and/or otherwise generated using generative adversarial networks (GANs), filter, etc. Detection occurs after the fact, while a prediction is determined before an event occurs. In certain examples, prediction occurs in real time (or substantially real time given system processing, storage, and data transmission latency) using available data.

Post-processing of predicted, detected, and/or classified events can include a dashboard visualization for detection, classification, and/or prediction. For example, post-processing can generate a visualization summarizing events. Post-processing can also generate notifications determined by detection, classification, and/or prediction, for example.

In certain examples, an algorithm can be used to select one or more machine learning algorithms to instantiate a network model based on aggregated pre-processed data and a target output. For example, a hybrid RL can be selected for decision making regarding which events to choose from a set of targeted events. A transformer network can be selected for parallel processing and accelerating event generation, for example. A graph neural network can be selected for interpreting targeted events and relations exploration, for example. The neural network and/or other AI model generated by the selected algorithm can operate on the pre-processed data to generate summarized events, etc.

In certain examples, data can be pre-processed according to one or more sequential stages to aggregate the data. Stages can include data ingestion and filtration, imputation, aggregation, modeling, and recommendation. For example, data ingestion and filtration can include one or more devices connected to a patient and used to actively capture and filter data related to the patient and/or device operation. For example, a patient undergoing surgery is equipped with an anesthetic device and one or more monitoring devices capturing one or more of the patient's vitals at a periodic interval. The anesthetic device can be viewed as a source of machine events (acted upon the patient), and the captured vitals can be treated as a source of patient data, for example.

Figure 5:
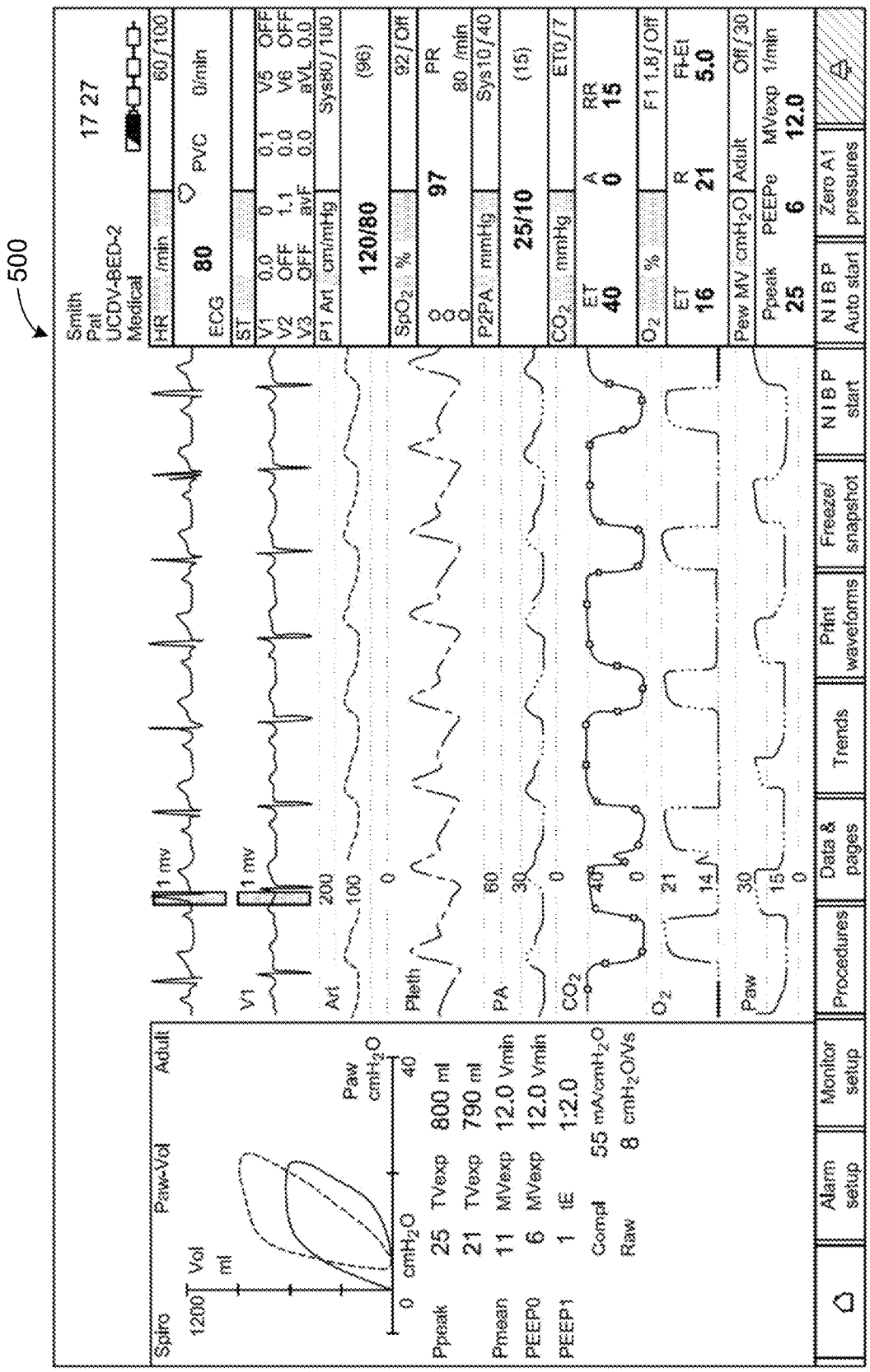
FIG. 5 illustrates an example visualization of data provided from multiple sources.

FIG. 5 illustrates an example visualization 500 of data provided from multiple sources including, an anesthetic device, a monitoring device, etc. Such a stream of data can have artifacts due to one more issues occurring during and/or after acquisition of data. For example, heart rate and/or ST segment errors can occur due to electrocautery interference, patient movement, etc. Oxygen saturation measurement errors can occur due to dislocation of a sensor, vasopressor use, etc. Non-invasive blood pressure errors can be caused by leaning on the pressure cuff, misplacement of the cuff, etc. Such artifacts are filtered from the stream using one or more statistics (e.g., median, beyond six sigma range, etc.) that can be obtained from the patient (e.g., current) and/or from prior records of patients who have undergone a similar procedure and may have involved one or more normalization techniques with respect to age, gender, weight, body type, etc.

In certain examples, the data may have some observation missing and/or removed during a filtration process, etc. This missing information can be imputed with data before being used for training a neural network model, etc. The data can be imputed using one or an ensemble of imputation methods to better represent the missing value. For example, imputation can be performed using a closest fill (e.g., using a back or forward fill with the value closest with respect to time, etc.), collaborative filtering by determining another input that could be a possible candidate, using a generative method trained with data from large sample of patients, etc.

In certain examples, a captured stream of data may involve aggregation before being consumed in downstream process(es). Patient data can be aggregated based on demographic (e.g., age, sex, income level, marital status, occupation, race, etc.), occurrence of a specific medical condition, etc. One or more aggregation methods can be applied to the data, such as K-means/medoids, Gaussian mixture models, density-based aggregation, etc. Aggregated data can be analyzed and used to classify/categorize a patient to determine a relevant data set for training and/or testing of an associated neural network model, for example.

For example, using K-means/medoids, data can be clustered according to certain similarity. Medoids are representative objects of a data set or a cluster with a data set whose average dissimilarity to all the objects in the cluster is minimal. A cluster refers to a collection of data points aggregated together because of certain similarities. A target number k can be defined, which refers to a number of centroids desired in the dataset. A centroid is an imaginary or real location representing a center of the cluster. Every data point is allocated to each of the clusters by reducing an in-cluster sum of squares, for example. As such, a K-means algorithm identifies k number of centroids, and then allocates every data point to the nearest cluster, while keeping the centroids as small as possible. The "means" in the K-means refers to an averaging of the data; that is, finding the centroid. In a similar approach, a "median" can be used instead of the middle point. A "goodness" of a given value of k can be assessed with methods such as a silhouette method, Elbow analysis, etc.

In certain examples, a Gaussian mixture model (GMM) is a probabilistic model that assumes all the data points are generated from a mixture of a finite number of Gaussian distributions with unknown parameters. A Gaussian mixture model can be viewed as generalized k-means clustering to incorporate information about covariance structure of the data as well as centers of latent Gaussians associated with the data. The generalization can be thought of in the shape the clusters are formed, which in case of GMMs are arbitrary shapes determined by Gaussian parameters of the distribution, for example.

Density-based spatial clustering of applications with noise (DBSCAN) is a data clustering algorithm that can be used in data mining and machine learning. Based on a set of points (e.g., in a bi-dimensional space), DBSCAN groups together points that are close to each other based on a distance measurement (e.g., Euclidean distance, etc.) and a minimum number of points. DBSCAN also marks as outliers points that are in low-density regions. Using DBSCAN involves two control parameters, Epsilon(distance) and minimum points to form a cluster, for example. DBSCAN can be used for situations in which there are highly irregular shapes that are not processable using a mean/centroid-based method, for example.

In certain examples, a recommender system or a recommendation system is a subclass of information filtering system that seeks to predict the "rating" or "preference" a user would give to an item. The recommender system operates on an input to apply collaborative filtering and/or content-based filtering to generate a predictive or recommended output. For example, collaborative filtering builds a model based on past behavior as well as similar decisions made by other users. This model is then used to predict items (or ratings for items) that the user may have an interest in. Content-based filtering approaches utilize a series of discrete, pre-tagged characteristics of an item to recommend additional items with similar properties. In the healthcare context, such collaborative and/or content-based filtering can be used to predict and/or categorize an event and/or classify a patient based on the event(s), etc.

Thus, certain examples provide a plurality of methods that can be used to determine a cohort to which the patient belongs. Based on the cohort, relevant samples can be extracted to train and inference a model for a given patient. For example, when looking at a particular patient and trying to inference for the particular patient, an appropriate cohort can be determined to enable retrieval of an associated subset of records previously obtained and/or from a live stream of data. In certain examples, a top N records are used for training and inferencing.

In certain examples, patients and associated patient data can be post-processed. For example, given that a clinician attends to more than one patient at a given point of time, patients and associated data can be summarized, prioritized, and grouped for easy and quick inferencing of events/outcomes.

For example, patients can be prioritized based on a clinical outcome determined according to one or more pre-determined rules. Patients can also be prioritized based on variance of vitals from a nominal value of the cohort to which the patient belongs, where the cohort is determined by one or more aggregation methods, for example.

Additionally, aggregation can be used to provide a high-level summarization of one or more patients being treated. Summarization can also involve aggregation of one or more events occurring in parallel for ease of interpretability. This process of summarization can also be modeled as a learned behavior based on the learning of how a clinician prefers to look at the summarization, for example.

As such, trained, deployed AI models can be applied to 1D patient data to convert the patient time series data into a visual indication of a comparative value of the data. For example, processing the 1D time series patient data using an AI model, such as one or more models disclosed above, quantifies, qualifies, and/or otherwise compares the data to a normal value or values, a threshold, a trend, other criterion (-ia) to generate a color-coded, patterned, and/or shaded representation of the underlying time series (e.g., waveform, etc.) data. Data can be clustered for a particular patient, and patients can be clustered for a particular group, such as a hospital, department, ward, clinician, office, enterprise, condition, etc.

Using the prioritization, patient(s) and event(s) can be determined from the group of available patients and events for which a clinician and/or healthcare system/device is to be notified for immediate attention, for example. In certain examples, a visualization can be generated from the prioritized data to enable understandable, actionable, display and interaction with the data.

Figure 6:
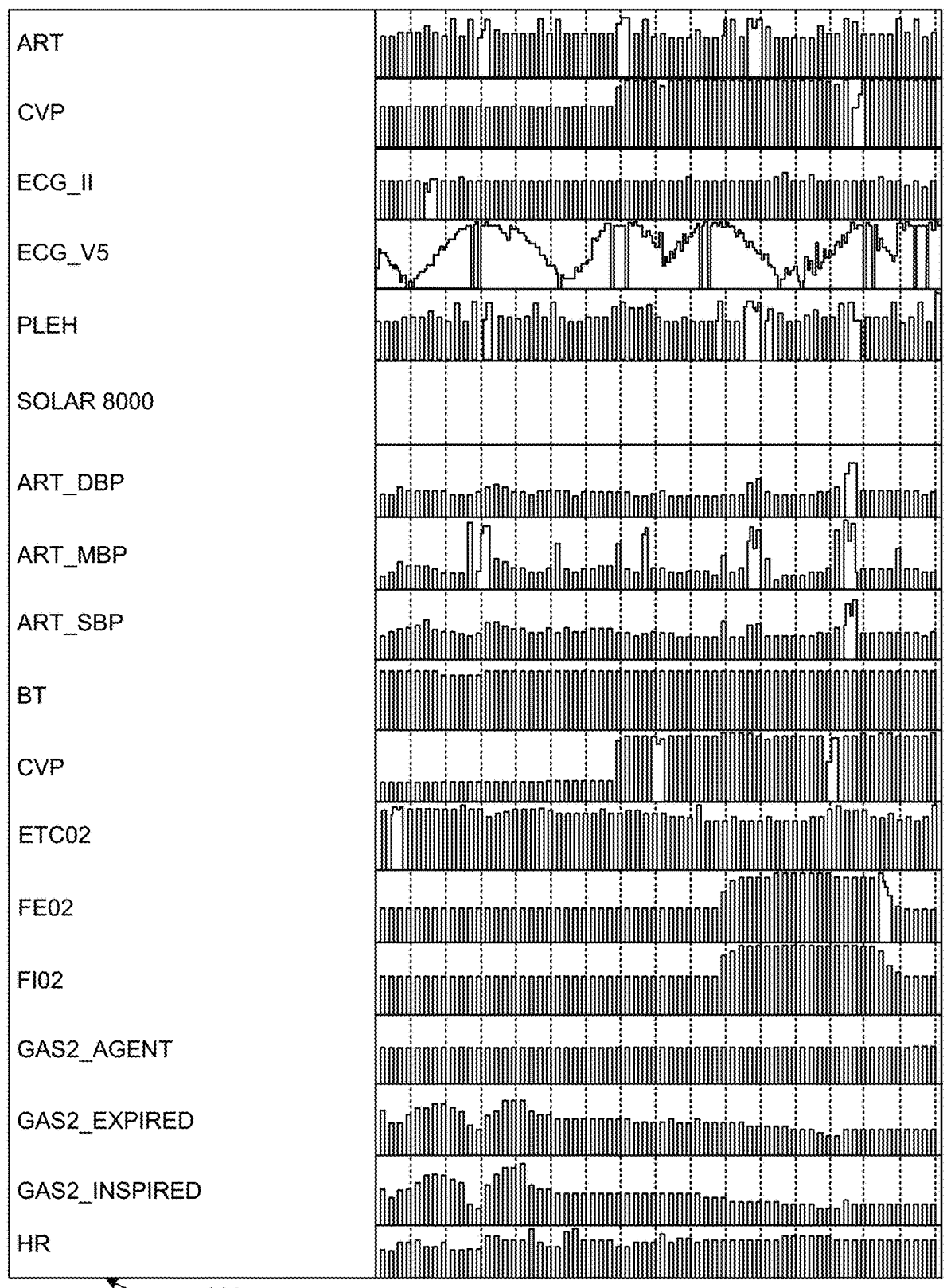
FIG. 6 illustrates an example interface displaying one-dimensional patient data for interaction and processing.

Thus, certain examples gather 1D time series (e.g., waveform) data from one or more medical devices (e.g., ECG, EEG, ventilator, etc.) and a patient via one or more monitoring devices. Physiological data and other 1D time series signals can be indicative of a physiological condition associated with a body part from which the data is obtained (e.g., because the signal corresponds to electrical activity of the body part, etc.). As such, the time series physiological signal data, machine data, etc., can be processed used by clinicians for decision making regarding a patient, medical equipment, etc. As shown in the example of FIG. 6, a variety of waveforms 600 (e.g., ECG, heart rate (HR), respiratory gas movement, central venous pressure, arterial pressure, oxygen fraction, waveform capnography, etc.) can be captured with respect to a patient for correlation, analysis, display, modeling, etc.

A data view, such as example data view 600, can be generated and provided for a particular patient from the gathered, processed data set, for example. In certain examples, the patient data can be normalized to provide a graphical representation of relative and/or other comparative values. For example, a normalized value can be converted from an alphanumeric value into a graphical representation of that value (e.g. a color, a pattern, a texture, etc.), and a group or set of values for a patient can be represented as a group or cluster of graphical representations (e.g., a set of colored lines, a combination of patterns and/or textures, etc.) in a block for that particular patient. Additionally, a graphical user interface can display and provide access to graphical representations for a set or group of patients shown together for visual comparison, interaction, individual processing, comparative processing, sorting, grouping, separation, etc. The graphical user interface (GUI) view of multiple patients can be organized/arranged according to one or more criterion (e.g., duration, location, condition, etc.).

In certain examples, such a GUI can arrange blocks or clusters of patient data such that each patient's block is distinct from other adjacent patient blocks. In certain examples, patient blocks or "cases" can be arranged around (e.g., anchored by, displayed with respect to, etc.) a normalization point or common event/threshold, such as an emergency start event, etc. For example, an occurrence of an emergency event, such as a stroke, heart attack, low blood pressure, low blood sugar, etc., can be indicated in each of a plurality of patients and used to normalize the patient data blocks with respect to that emergency event.

Figure 7:
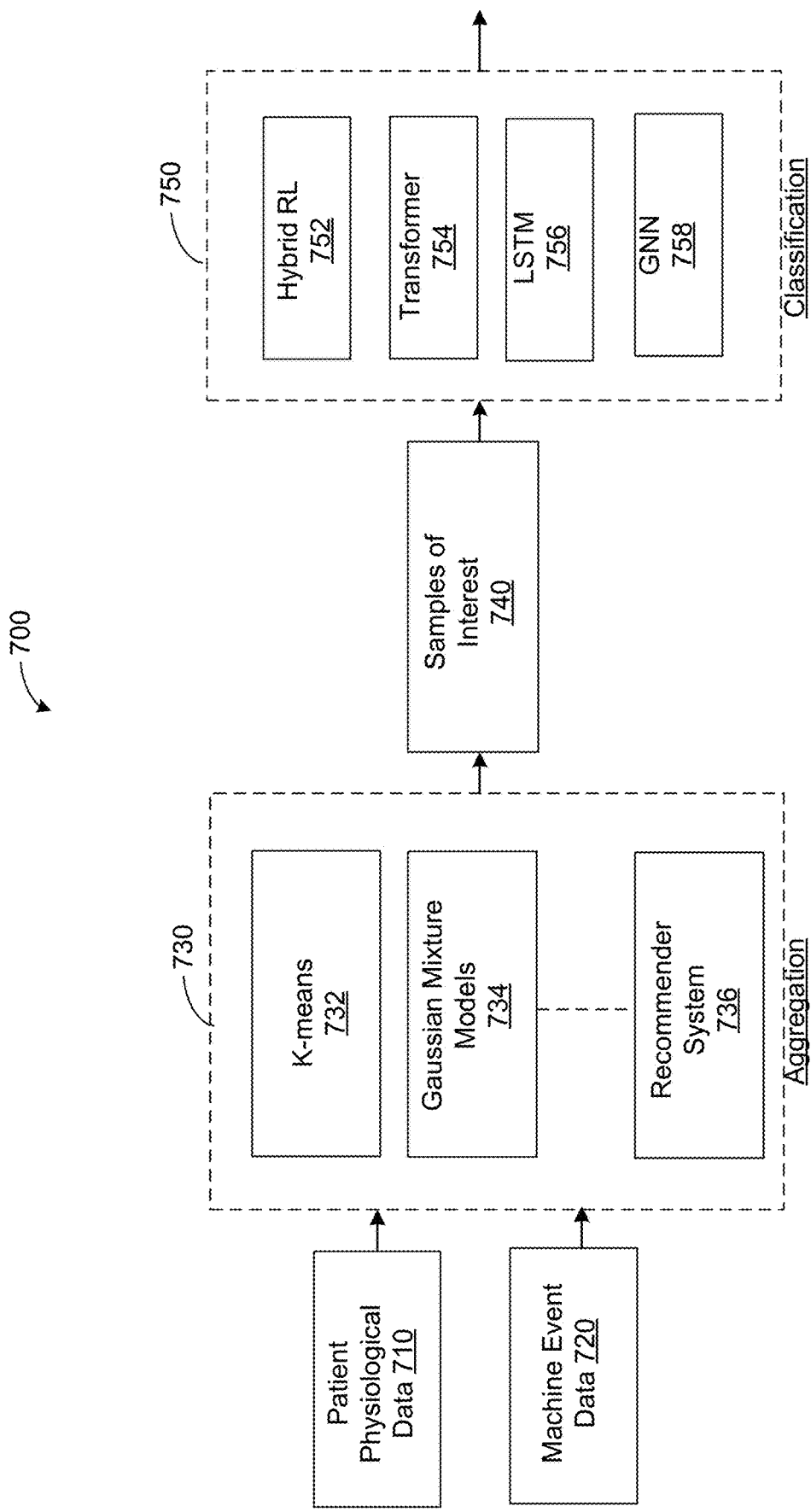
FIG. 7 illustrates a schematic of an example system to predict medical machine events using patient waveform data.

FIG. 7 illustrates a schematic of an example system 700 to predict medical machine events using patient waveform data. The example system or apparatus 700 includes patient physiological signal data 710 and medical machine event data 720 provided to an aggregator 730. The aggregator 730 includes a plurality of models 732-736 to aggregate data 710, 720 into samples of interest 740 for processing by a classifier 750 to classify the data using one or more AI models 752-758 to provide a classification output. As shown in the example of FIG. 7, the aggregator 730 includes one or more models 732-736 to cluster/aggregate the gathered data 710, 720. For example, the data 710, 720 can be aggregated based on demographic (e.g., age, sex, income level, marital status, occupation, race, etc.), occurrence of a specific medical condition, etc. One or more aggregation methods can be applied to the data 710, 720, such as K-means/medoids 732, Gaussian mixture models 734, density-based aggregation, etc. Aggregated data can be analyzed and used to classify/categorize a patient to determine a relevant data set for training and/or testing of an associated neural network model, for example.

For example, the K-means/medoids 732 can cluster the data 710, 720 according to certain similarity. The Gaussian mixture model (GMM) 734 can be used to cluster the data 710, 720 according to arbitrary cluster shapes determined by Gaussian parameters of the distribution of the data 710, 720, for example. Other models, such as DBSCAN, etc., can be used to aggregate the data 710, 720. One or more models 732-734 can be selected or activated to the process the data 710, 720. In certain examples, the recommender system 736 predicts a ranking, rating, or preference associated with the data 710, 720, output of a model 732, 734, etc. The recommender system 736 processes the input data 710, 720 and output of the model 732, 734 to apply collaborative filtering and/or content-based filtering to generate a predictive or recommended output. For example, collaborative filtering builds a model based on past behavior as well as similar decisions made by other users. This model is then used to predict items (or ratings for items) that the user may have an interest in. The predicted output provides one or more samples of interest 740 for further processing to predict and/or categorize an event and/or classify a patient based on the event(s), etc.

The example classifier 750 of FIG. 7 is used to apply one or more AI models to the data samples of interest 740. For example, the classifier 750 can be configured, selected, triggered, and/or otherwise determined to apply a hybrid RL network model 752, a transformer network model 754, an LSTM network model 756, and/or a GNN model 758 to one or more of the samples of interest 740. The AI model 752-758 applied can depend on a task associated with the request for data processing via the apparatus 700, an input source for the data 710, 720, a target for the classification and/or other predictive output, etc.

For example, the apparatus 700 can be used to predict one or more future medical machine events and summarize pertinent past medical machine events related to the predicted one or more future medical machine events using a consistent input of time series data related to a patient. Certain examples can provide a healthcare provider-facing interface of an electronic device for use by a healthcare provider treating the patient configured to display the predicted one or more future medical machine events and the pertinent past medical machine events of the patient. Certain examples can provide a healthcare provider-facing interface for an electronic device for use by a healthcare provider treating the patient. The device and associated interface are configured to automatically calibrate a monitoring system monitoring the patient to extract the 1D signal data 710, 720 using the model(s) 752-758. Patient health, machine health, device calibration, etc., can be driven through prediction, detection, and/or classification of events using one or more of the models 752-758, for example. Metadata extracted from gathered data 710, 720, associated machine configuration information, etc., can be used to select one or more model(s) 752-758 as appropriate to analyze certain data 710, 720, predict certain events, classify certain conditions, etc. Selected model(s) 752-758 then map to selected data points 740 from the set of data 710, 720, for example.

The aggregator 730 can be used to select a relevant data cohort through partitioning, grouping, etc., according to one or more unsupervised clustering methods 732, 734, using the recommender 736 to sort prior records and use a top-n closest records of a current data sample to form the samples of interest 740. Data aggregation can be task-dependent, such as for a particular product, particular task, etc.

Thus, certain examples provide a plurality of methods that can be used to determine a cohort to which the patient belongs. Based on the cohort, relevant samples can be extracted to train and inference a model for a given patient. For example, when looking at a particular patient and trying to inference for the particular patient, an appropriate cohort can be determined to enable retrieval of an associated subset of records previously obtained and/or from a live stream of data. In certain examples, a top N records are used for training and inferencing.

Example Hybrid Reinforcement Learning Medical Events Prediction Framework

For example, reinforcement learning (RL) and/or hybrid RL learning model 752 can be used to form a medical events prediction framework. RL is a type branch of AI centered around an environment that senses, observes and interacts with an agent in the environment. The environment, in turn, either rewards the agent or does not based on certain conditions to attain a specific goal. RL can be implemented using a model-free (direct) approach and/or a model-based (indirect) approach. The model-free method is a direct approach based on trial and error of experiences. The model-based method is based on a model representation of the environment, such that an agent can predict the next state and/or reward from past experiences. Planning is a problem-solving method to determine an optimal policy given the model of the environment.

Planning involves computation of a value function to find an optimal policy backed up by values from simulated experiences. Planning efficiency is dependent on the model choosing the right states and actions that result in an optimal, preferred, or other beneficial solution. The exact model of the environment and interactions between the agent and its environment drive the model's success. However, in practical applications, the exact model of the environment is not known, which leads to model errors. Successful model-based reinforcement learning applications are not widely available, as each environment needs to be modelled in detail to capture its dynamics accurately. Modelling application environments for this purpose can be cumbersome and, as a result, limit the application of reinforcement learning. To overcome this difficulty, certain examples provide innovative methods with detailed planning in spatial and/or temporal contexts. Such spatial and/or temporal contexts can be applied using model-based (MB) and model-free (MF) approaches to the healthcare domain to drive innovative solutions.

The need for lowering costs and improving quality in healthcare is imperative across the globe. Operating Room (OR) costs are one of the significant portion of the hospital's costs. There are many sequential decision-making steps involved in the OR functioning. Examples of OR decisions are transferring patients to post-anesthesia care units (PACU), scheduling staff for PACU, determining surgery end, estimating emergence phase, time to extubate, and critical event alarms. OR medical devices such as anesthesia machines, ventilators, monitoring systems are rich source of time-series data that help in processing, identifying, and alerting events that in turn serve as basis for optimal decision making. Most of the techniques that use RL are MF approaches, where there are no assumptions of the environment or data samples required to learn a policy. Such approaches are often flexible and learn complex policies effectively, but require many trials and training time for convergence. On the contrary, MB approaches require lot of data samples and less training time to converge faster. Though practically efficient, model-based approaches are sensitive to biases. As such, certain examples combine MB and MF data-driven medical events prediction into a hybrid RL framework.

Under such architecture, a model learns from experience by MF and predicts rewards/state values using MB that are used in learning value functions or policy. By including a learned model, hybrid RL accelerates the overall training time since the learned model exploits the environment. Robust functional approximation can be used for training and definition of the environment, for example.

Certain examples provide a hybrid RL system applicable to event prediction and/or analysis in an OR and/or other healthcare setting. For example, the hybrid RL system can be applied to predict an end of surgery event for planning staffing and patient transfer to the PACU. The hybrid RL system can be used to identify ventilator asynchrony and predict when the patient is able to breathe by themselves. The hybrid RL system can also predict a time to extubation. The hybrid RL system can be used for emergence prediction, such as to predict when a patient wakes up post turning off anesthesia. The hybrid RL system can be used for false alarm prediction to predict anomalies during surgeries such as false alarms, etc., to avoid alarm fatigue.

Certain examples provide a hybrid RL framework including an MB component that can be built based on available historical data sets and a MF component to be explored as new data is received to improve efficiency of the RL agent. Such a hybrid RL approach enables learning from the available historical data and building an efficient algorithm combining the strengths of both MB and MF to learn a better policy, for example.

For example, the hybrid RL framework, such as the hybrid RL framework 430 of FIG. 4D, can be used to predict extubation time in patients in an intensive care unit (ICU) of a hospital. Moderating sedation levels for critically ill patients, especially patients on mechanical ventilation in an ICU, is a very complex problem space and critical for a safe treatment of patients. Closed-loop control of anesthesia can enable positive outcomes such as early recovery, patient safety and reduced treatment costs. Optimal drug dosage requires consideration of several factors such as physiological conditions, drug interactions, drug residual effects, inter-patient variability, and medical device characteristics. Over or under sedation side effects can lead to adverse events. Open-loop control is time consuming and expensive. In the case of ICU patients on ventilators, moderation of multiple drugs to control multiple physiological variables is imperative and involves a complex model that focus on pharmacokinetics and pharmacodynamics, for example.

Many predictive controller algorithms and uncertainty modeling experience challenges when accommodating external disturbances and long varying variables. Adaptive controller algorithms that can model the changing variables and external disturbances might work but have deficiencies that need to be addressed. An RL framework that needs no assumptions of system dynamics addresses the problem of finding optimal or desirable solutions in this complex problem space.

Figure 8:
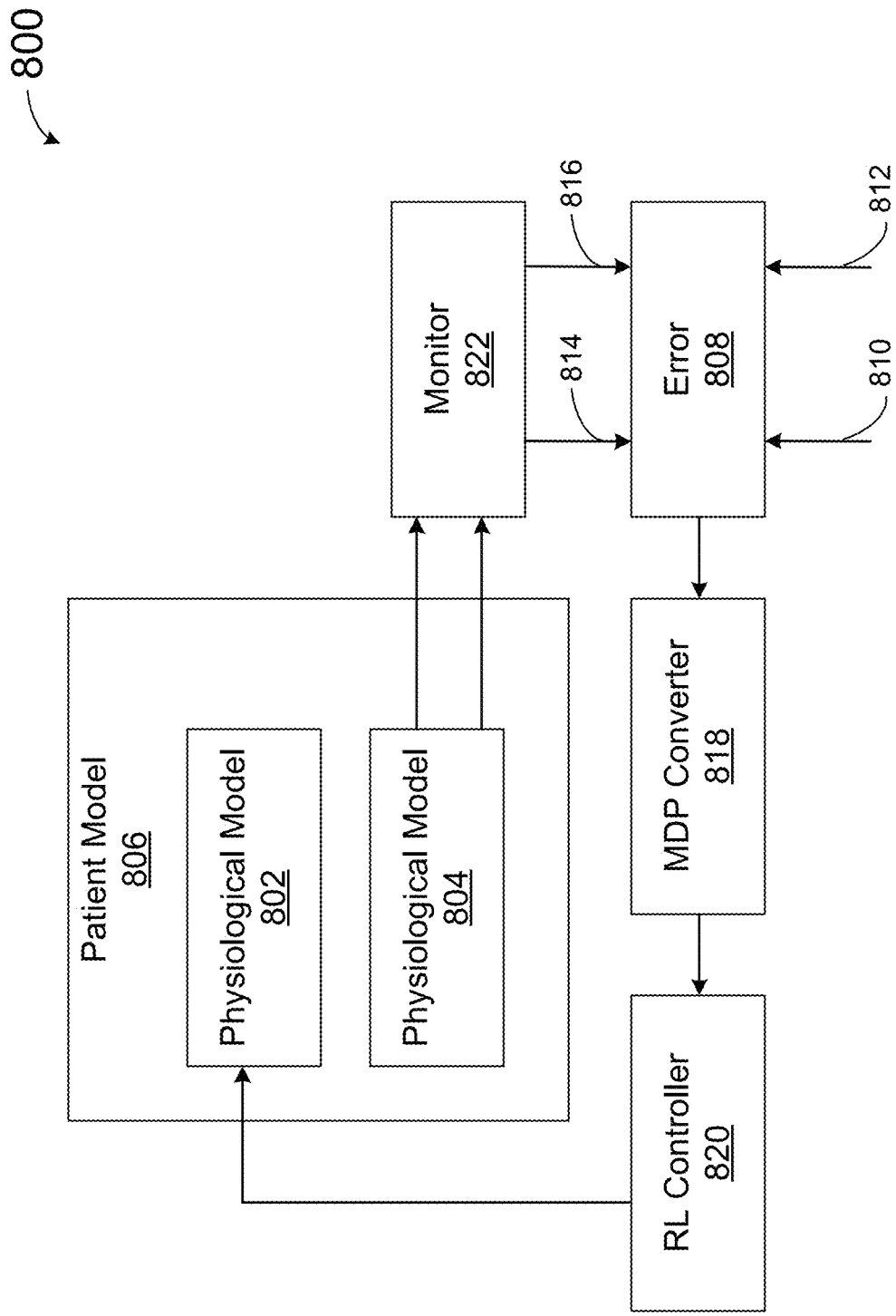
FIG. 8 illustrates an example system to train a reinforcement learning agent.

In certain examples, a patient model is used to train an RL agent as shown in FIG. 8. In the example of FIG. 8, a closed-loop Q-learning algorithm is used to monitor (e.g., analyze to detect, classify, predict, etc.) bispectral index (BIS) and mean arterial pressure (MAP) values by monitoring infusion of an anesthetic such as propofol, etc., and correlating the monitored anesthesia with other patient events (e.g., beginning of surgery, end of surgery, patient distress, etc.). An anesthetic infusion rate is learned from simulations run on a first physiological model 802 and a second physiological model 804 for a patient 806. The infusion rate is calculated as shown below in Equation 1, where $k \in \{1, 2, \ldots\}$, $IR_{max}$ is a maximum infusion rate, and $a_k$ is an action at a $k^{th}$ step that can vary between 0 (no infusion) to 1 (maximum rate):

$$IR_k = a_k \times IR_{max} \qquad \text{(Equation 1)}.$$

Action is taken based on a current state of the environment, which is observed as a difference of error 808 between target 810, 812 and measured 814, 816 values of BIS and MAP, respectively. The error values can be formatted as a finite Markov Decision Process (MDP) representation 818 to be provided to an RL agent/controller 820. A goal of the RL agent or controller 820 is to minimize (or otherwise reduce) the error. Simulated values of BIS and MAP errors are calculated based on propofol concentrations using the physiological model 804. One or more monitors 822 capture measured BIS 814 and MAP 816 values as a function of kT, in which k represents a time step and T is a factor or "temperature" that influences randomness in the function. The actions that give lowest error difference between measured 814, 816 and target 810, 812 BIS and MAP values get the highest reward. If a current time step error is higher than the prior current time step error, then the reward is zero, penalizing the current action taken. The RL agent 820 learns possible combinations of states and actions taken to observe the responses. The "optimal" or desirable policy learnt using an E greedy policy from the simulations is used for evaluating the performance.

As patient safety is involved in clinical applications, certain examples provide a closed-loop patient safe anesthesia control using an MB RL approach. One limitation with this approach can occur when there is significant variance in real time parameter values from the nominal value of the patient model. This occurrence can be addressed by updating the policy with the new Q values and occasionally exploring then exploiting. Since this is a patient safety problem space, random actions or exploration is not practical. Therefore, a more generalized approach such as functional approximators or batch model RL can be applied where fewer interactions with the system are required for a good policy. Addressing drug response delays and patient variables such as weight, age, gender can cause variances in the parameters that are different than the trained patient model. Certain examples apply one or more RL agents to a range of drug infusion rates with various patient characteristics. Control techniques using a continuous state action space can be used to address the limitation of discrete action and state space, for example.

The usage of mechanical ventilation has increased as healthcare advanced and survival rates increased. Mechanical ventilation is used for patients with acute respiratory failures due to surgery or underlying medical condition. ICU studies show that 12% of the hospital's costs are attributed to the usage of mechanical ventilators. Early extubation or prolonged extubation has many side effects such as patient discomfort of reintubation, inflating hospital resources and ventilator asynchrony. There is a need for optimal extubation protocol personalized based on individual patient condition. While an off-policy RL approach to determine an optimal weaning policy from historical data may be useful, there are several challenges with the historical data such as sparsity, noise due to artifacts, and interval censoring where there is an interval range than an absolute observation, for example. For example, interval censoring is a challenge to learn a policy and its evaluation. Further, with the off-policy RL approach, the time to extubate is only available as upper bound and not the exact time.

A mechanical weaning problem can be formulated into an MDP where there is a finite state space of patient states (e.g., physiological signals) at every time step t. A transition probability function given the current state and actions taken. An action space at each time step t that influences patient state to move to next step and a reward function for each transition. The main goal of the RL agent is to learn a policy which is a mapping of states to actions that maximizes the reward as shown in below equation. The rewards are discounted as per γ to differentiate between immediate versus long-term reward.

$$R^\pi(s_t) = \lim_{T \to \infty} E_{s_{t+1}|s_t, \pi(s_t)} \sum_{t=1}^{T} \gamma^t r(s_t, a_t).$$ (Equation 2)

The state space, $s_t$, variable at each time step t includes, for example, thirty-two features ranging from patient demographics, physiological variables, ventilation settings, sedative dosages, time of intubation, and number of times intubated, for example. An action space in the example includes eight finite actions combined using two actions for ventilator on/off and four sedation levels. A reward signal is defined as a combination of sigmoid, piecewise-linear, and threshold functions of the subset vitals and successful extubation and penalties for adverse events.

In certain examples, a fitted q-iteration (FQI) off-policy MF approach is used to functional approximate the q-values of a state action pair. Since FQI is a MF method, there are no assumptions of the system dynamics, and tuple samples are independent and identically distributed (i.i.d.). The Q-function in FQI is updated after each iteration as shown below:

$$\hat{Q}_k(s, a) \leftarrow r_{t+1} + \gamma \max_{a \in A} \hat{Q}_{k-1}(s_{t+1}, a),$$ (Equation 3)

where $\overline{Q}_1(s,a) = r_{t+1}$ (Equation 4).

An optimal policy after k iterations can be given by:

$$\pi^*(s) = \arg\max_{a \in A} \hat{Q}_k(s, a).$$ (Equation 5)

In certain examples, MF approaches can be flexible and learn complex policies effectively, but their global convergence requires large number of trials resulting in a high computational costs and training time. On the contrary, model-based techniques have strong theoretical basis, and generalize better if the dynamics of the system is known as seen in the closed-loop control of propofol above. Though practically efficient, model-based approaches are sensitive to biases in the model. In addition, it is difficult to know the dynamics of the model. Thus, both of the aforementioned approaches have their own advantages and limitations. Considering the advantages of both techniques, certain examples provide a hybrid RL framework to bridge the gap between MB and MF approaches.

Many MB models of RL have focused on the spatial and temporal dynamics independently. That is, variations in the spatial dimension or temporal dimension alone are researched for RL applications. The combined spatial and temporal dynamics of RL investigations are very limited, and yet are necessary for a realistic representation of the problem worlds.

Dynamic Mode Decomposition (DMD) can be used to analyze neural recording data, for example. DMD extracts both spatial and temporal modes of the data simultaneously and captures the primary objectives of Principal Components Analysis (PCA) used for spatial data and power spectral analysis, for a temporal data which are traditional approaches used for analyzing large-scale neural recordings. DMD algorithms can be used to combine spatial and temporal patterns extraction. DMD is found to be robust for different samples and can efficiently predict a system's dynamics. A DMD algorithm captures the spatial and temporal modes of a system dynamics effectively, which is helpful in building an accurate environment model. DMD captures the dynamics of the system, which can be a potential approach to building an environmental model for real-world applications that involves both spatial and temporal features. If the model of the problem world is built such that it abstracts the dynamics closest to reality, then the accuracy of the model will improve, thereby increasing planning efficiency, for example.

Certain examples provide data-driven prediction framework using reinforcement learning for time-series data generated by medical devices and/or patient monitoring systems to drive detection, classification, and prediction of events for improved decision-making regarding patient care and improved maintenance of medical devices, monitoring systems, and other equipment. Certain examples provide a framework that is generalized for any medical time-series data and medical events prediction, such as end of surgery, beginning and end of anesthesia, stroke, heart attack, etc.

Certain examples provide a hybrid RL network model to learn and generate an improved policy for a large state space with a sparse reward signal including efficient sampling of experiences that lead to high reward states. The hybrid RL model identifies state-action pairs that lead to high rewards.

Certain examples provide a hybrid RL system that performs (e.g., provides accuracy) and scales better than a system that provides an MF-only or MB-only solution. Certain examples provide faster convergence than a MF-only or MB-only solution. Certain examples provide improved generalization across use-cases and improved interpretation of results. Certain examples integration MB-based RL methods and MB-based RL methods to form a hybrid RL system for efficient policy learning in the healthcare domain.

Certain examples provide a prediction framework based on hybrid RL and deep learning methods to predict medical events to enable healthcare providers to make optimal or otherwise improved decisions. Medical events in this context are described as events generated from medical machines such as anesthesia, ventilators, etc., and/or physiological data generated by patients and captured via monitoring systems, for example. Captured data can be pre-processed for different sampling frequencies, and missing values in the 1D signal data series can be imputed before being input to the hybrid RL framework, for example.

Figure 9A:
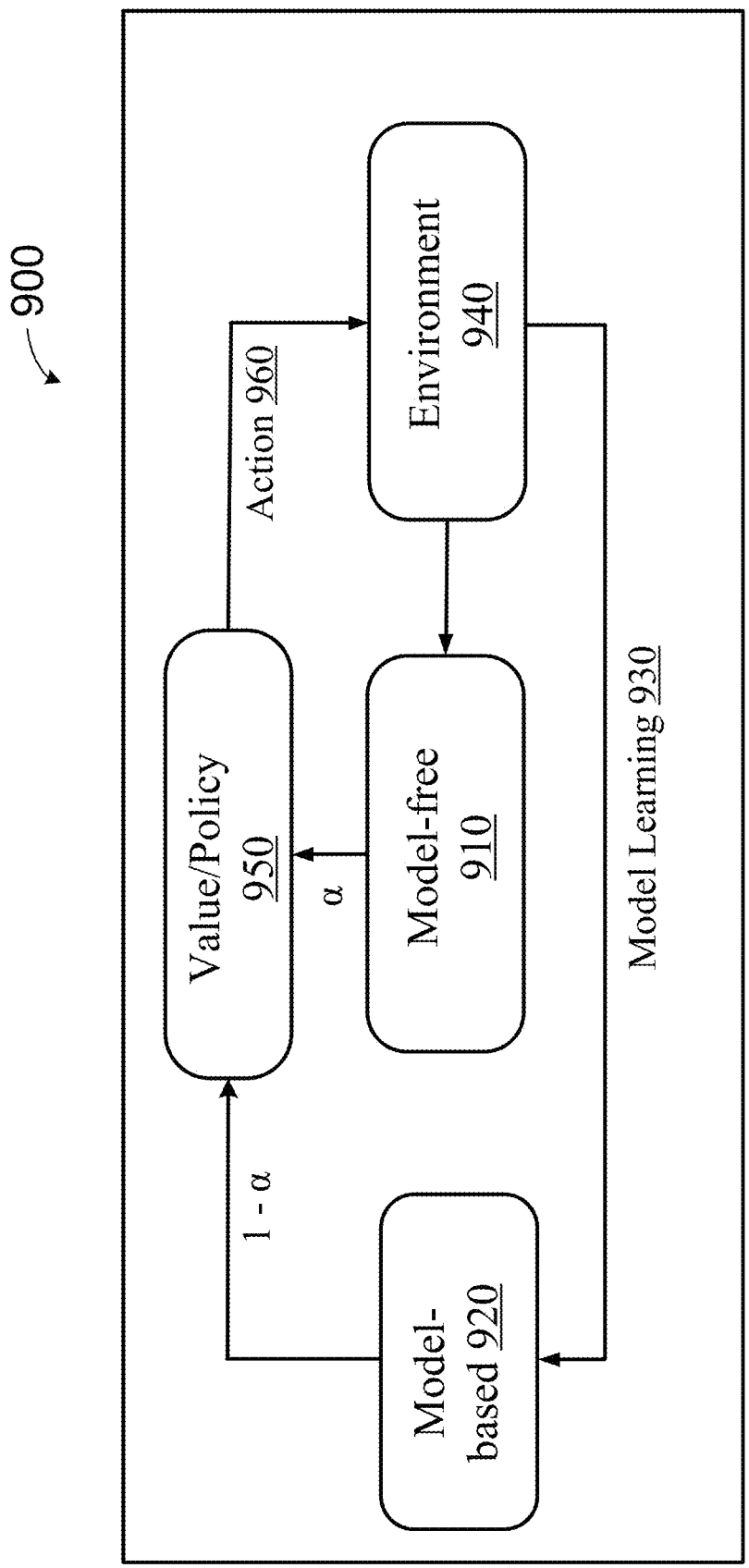
FIG. 9A is a schematic of a hybrid reinforcement learning framework.

FIG. 9A is a schematic of an example hybrid RL system, apparatus, or framework 900. The example system 900 includes a model-free (MF) processor 910 (also referred to as a model-free component of the hybrid RL system 900) and a model-based (MB) processor 920 (also referred to as a model-based component of the hybrid RL system 900). As shown in the example of FIG. 9A, the MB processor 920 is built using samples 930 collected from experiences in a monitored environment 940. A Markov decision process (MDP) the RL system 900 is defined by a finite state space S in which, at each time step t, the environment 940 transitions to a next state $s_t \in S$. The vector $s_t$ is a vector of all patient/machine variables at a given time t, for example. The MDP is also defined by an action space A in which an agent takes an action $a_t \in A$ at each time step that influences $s_{t+1}$. Actions can include time to extubate, raise an alarm, notify an event, etc. In some examples, the actions are classified as alarm or non-alarm (e.g., 1, 0, etc.). The example MDP is also defined by a reward function $r(s,a) \in R$ that is computed from a combination of input variables of patient state and action taken/not taken. For example, a scalar reward value of 1 is provided for a non-alarm; a scalar reward value of 10 is provided for a critical, clinically significant alarm, and a scalar reward value of 0 is provided for a wrong choice. A goal of the RL system 900 is to maximize an expected perceived reward by using known examples to learn an optimal/improved policy, for example.

The MB processor 920 can be designed as a deep neural network (DNN) architecture or DMD approach that captures non-linear system dynamics from historical data, for example. DMD can generalize better across datasets and reduce noise, which can be a significant challenge in time-series data. DMD with control (DMDc) integrates an effect of control to extract low-order models from high-dimensional complex time-series systems with actuation. DMDc can be represented as state space and control as shown in Equation 6 below, in which a future state $x_{k+1}$ is dependent on a current state $x_k$ and a current control $u_k$:

$$x_{k+1} = Ax_k + Bu_k \quad \text{(Equation 6)}.$$

The same equation without actuation, $u_k=0$, can be applied for datasets with no control. A functional approximation of A represents dynamics and eigen vectors of an underlying system being modeled. DMD is a data-driven equation-free method that accurately represents high-dimensional complex dynamics of the system being modeled. As such, in certain examples, DMD is used to implement the MB processor 920 in the hybrid RL medical event prediction framework 900.

The MF processor 910 of the framework 900 can be implemented as a Q-learning processor, an actor-critic functional approximation RL processor in which system assumptions are not required, etc. Alpha (a), as shown in the example of FIG. 9A, is a configurable parameter allowing the system 900 to choose between the MB processor 920 and the MF processor 910. When collecting new experiences, a higher value of a can be selected to leverage the MF processor 910 (e.g., where a E [0,1]). Once enough samples have been collected to generalize for a data set, the MB processor 920 can be activated to perform at expected minimum mean square error (MSE). Convergence times varies depending on activation of the MB 920 or MF 910. Training time can be faster with a stable MB processor 920, for example.

The example framework 900 is designed to predict medical events from learning an optimal event policy 950 using historical data and/or input from the MF processor 910 and/o the MB processor 920. Based on the value or policy 950 determined, an action 960 can be provided to the environment 940. The environment 940 senses, observes, and interacts with an RL agent in the environment 940. The environment 940 rewards or penalizes the RL agents (e.g., represented in model learning 930, etc.) to attain a specific goal. Policy results 950 can be evaluated using various performance metrics and statistical rigor. As such, the example hybrid RL system 900 can implement task automation with a goal-oriented action and sequential decision-making, for example.

The healthcare domain demands model interpretability as it involves human safety. Techniques such as saliency maps, activation heat maps and visualization techniques have been developed to explain model predictions to gain users trust. A combination of such techniques can be used to verify and explain hybrid RL model predictions for a selected use-case.

Thus, the example hybrid RL framework 900 includes data, models, and evaluations. The data can be pre-processed after acquisition from a data source (e.g., patient monitor, medical device, medical record system, etc.). In model development, the data can be split into training and testing data sets. Training data set(s) is/are used to train MB, MF, and hybrid RL models independently. The trained models can be tested for a hypothesis using the testing data set(s). Models can then be deployed that capture system dynamics of the environment 940 with high accuracy with the dynamics abstracted close to reality. The integrated model-free and model-based approach provides improved accuracy for predicting medical events using time-series data generated from medical machines such as anesthesia, ventilators, monitoring systems, etc. The integrated approach enables improved outcomes in clinical applications, for example.

Healthcare data suffers from both noise and lack of ground truth. As a result, the cost of data increases as it is cleaned and annotated in healthcare. Unlike other data sets, medical data annotation, which is critical to accurate ground truth, requires medical domain expertise for a better patient outcome. As such, the hybrid RL framework 900 can apply reinforcement learning to mimic the decision making process of annotators for medical events to automate annotation and labelling, for example. The reinforcement agent learns to annotate alarm data based on annotations done by an expert, for example. The reinforcement network 900 can then annotate alarm data and/or other types of medical event data once trained and tested, for example.

Figure 9B:
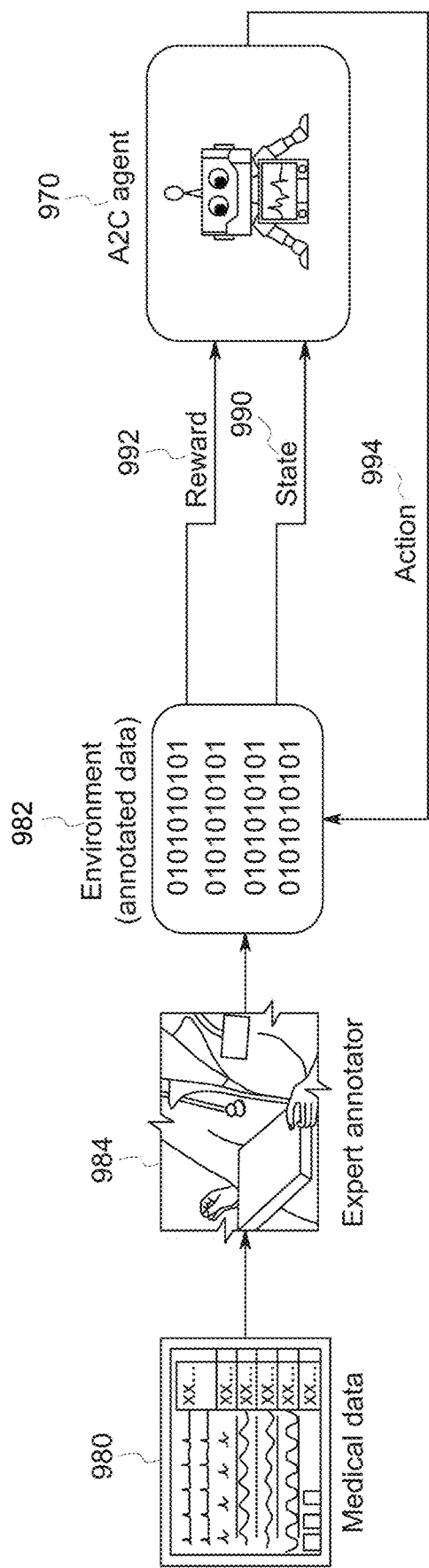
FIG. 9B depicts an example implementation of a hybrid reinforcement learning agent generated and deployed based on the example hybrid framework of FIG. 9A.

For example, FIG. 9B depicts an example implementation of a hybrid RL agent 970, generated and deployed based on the example hybrid RL framework 900, into which medical data 980 is annotated 982 by an annotator 984. The annotated medical data 982 is provided as a state 990 and associated reward 992 to the agent 970, which generates an action 994 back to the annotated data 982 after processing the state 900 and reward 992, for example. Thus, the agent 970 can process annotated data to identify alarms and non-alarms based on the state 990 represented by patient physiological signals generated by monitoring devices, such as electrocardiogram waveform data, pulse oximetry waveform data, vital signs (heart rate (HR), respiratory rate (RR), systolic blood pressure (SBP), diastolic blood pressure (DBP), mean arterial blood pressure (MAP), peripheral capillary oxygen saturation (SpO2), etc.), alarm messages (e.g., institution-specified alarms, protocol-specified alarms, etc.). The agent 970 can trigger an action 994 to correct when an alarm is identified, for example.

Clinical significance and clinical severity can be evaluated by the agent 970 based on the alarm(s). For example, alarm messages may be clinically significant (e.g., signifying improvement or deterioration of a condition, etc.). An event can also have no clinical significance or be of indeterminate clinical significance based on analysis by the agent 970, for example. Clinical severity evaluated by the agent 970 can include emergent, urgent, non-urgent, indeterminate, etc.

In certain examples, data analyzed by the agent 970/ framework 900 can be preprocessed and resampled in second, milliseconds, etc. The data can also be imputed using a determined mean value, etc., to forward fill the resampled data. Data from bedside monitors, other patient monitors, etc., including vitals, annotations, alarms, etc., can be preprocessed to convert alarms and annotations to on-hot encoding for processing, for example. Annotations can be divided into two categories of actions (e.g., alarms and non-alarms, etc.), for example. In certain examples, clinically significant and severe alarms (e.g., emergent, urgent, etc.) are categorized as an alarm, and indeterminate and non-urgent evens are categorized as a non-alarm. Processed vitals, alarms, and annotations can be merged (e.g., using a left join operation, etc.) to form a flattened file structure for model training, for example.

In certain examples, mapping (e.g., a Q-function, etc.) between actions and states is an important part of reinforcement learning. Actions can be learned using value-based methods and/or policy-based methods, for example. For example, the Q-function of Equations 3-5 can be used to determine an optimal/improved policy $\pi^*$ after k iterations. Alternatively or in addition, two networks can be used, with one network to learn an advantage value of taking an action (e.g., actor network) given a state s and a second network to learn the goodness of the action (e.g., critic network) as shown in Equation 3. The advantage value of the action given state s can be determined as follows:

$$A(s_t, a_t) \leftarrow r_{t+1} + \gamma V_v(s_{t+1}) - V_v(s_t) \quad \text{(Equation 7)}.$$

The optimal policy after k iterations is given by:

$$\pi_\theta(s,a) = P(a|s,\theta) \quad \text{(Equation 8)}.$$

Thus, certain examples generate and train hybrid RL and/or other AI models that learn and mimic domain expertise to automatically analyze and annotate critical alarms and trigger associated action, etc., while weeding out, ignoring, or not identifying false alarms.

Figure 10A:
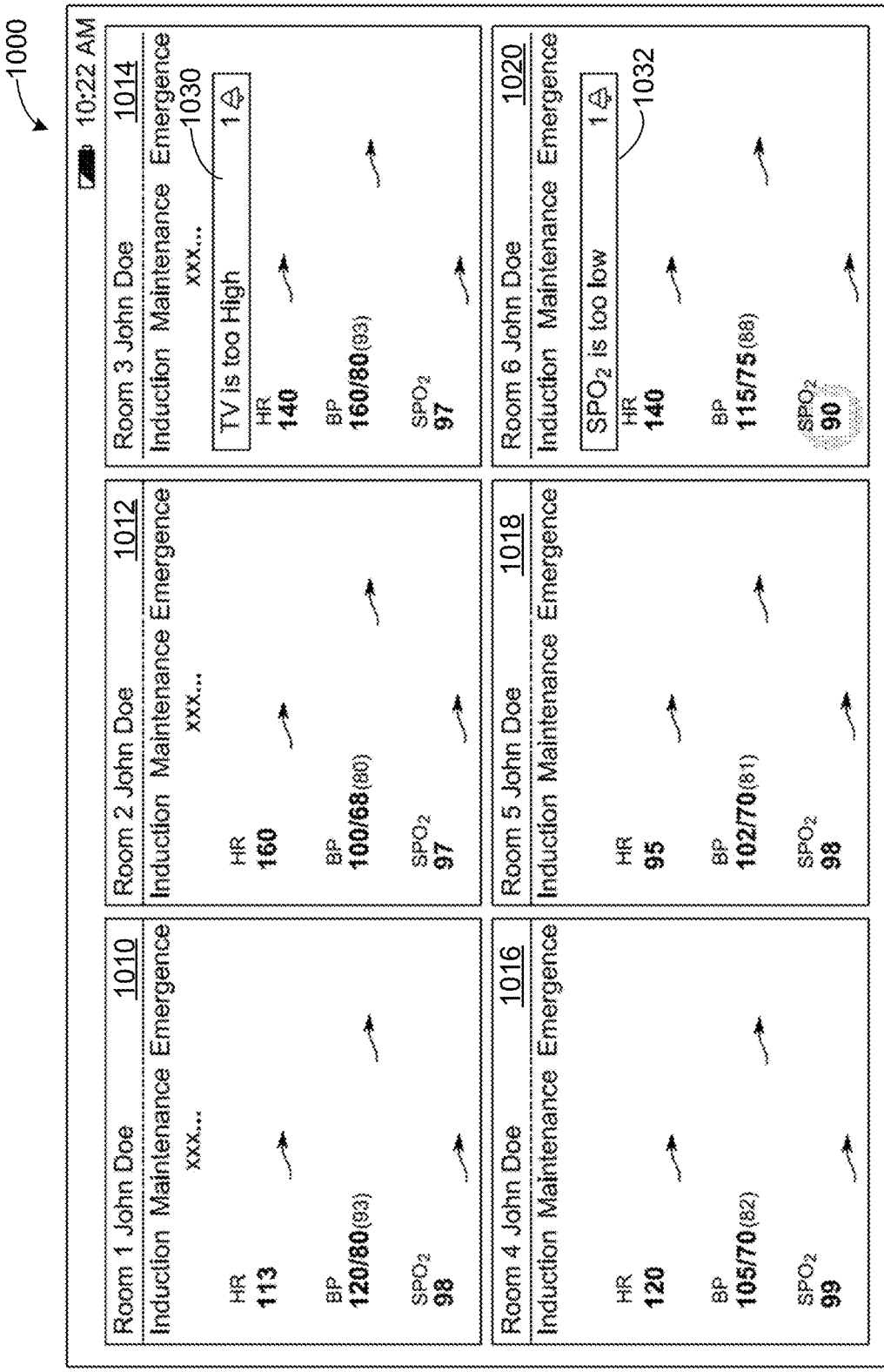
FIGS. 10A-10B illustrate example interfaces displaying one-dimensional patient data and associated analysis for interaction and processing.
Figure 10B:
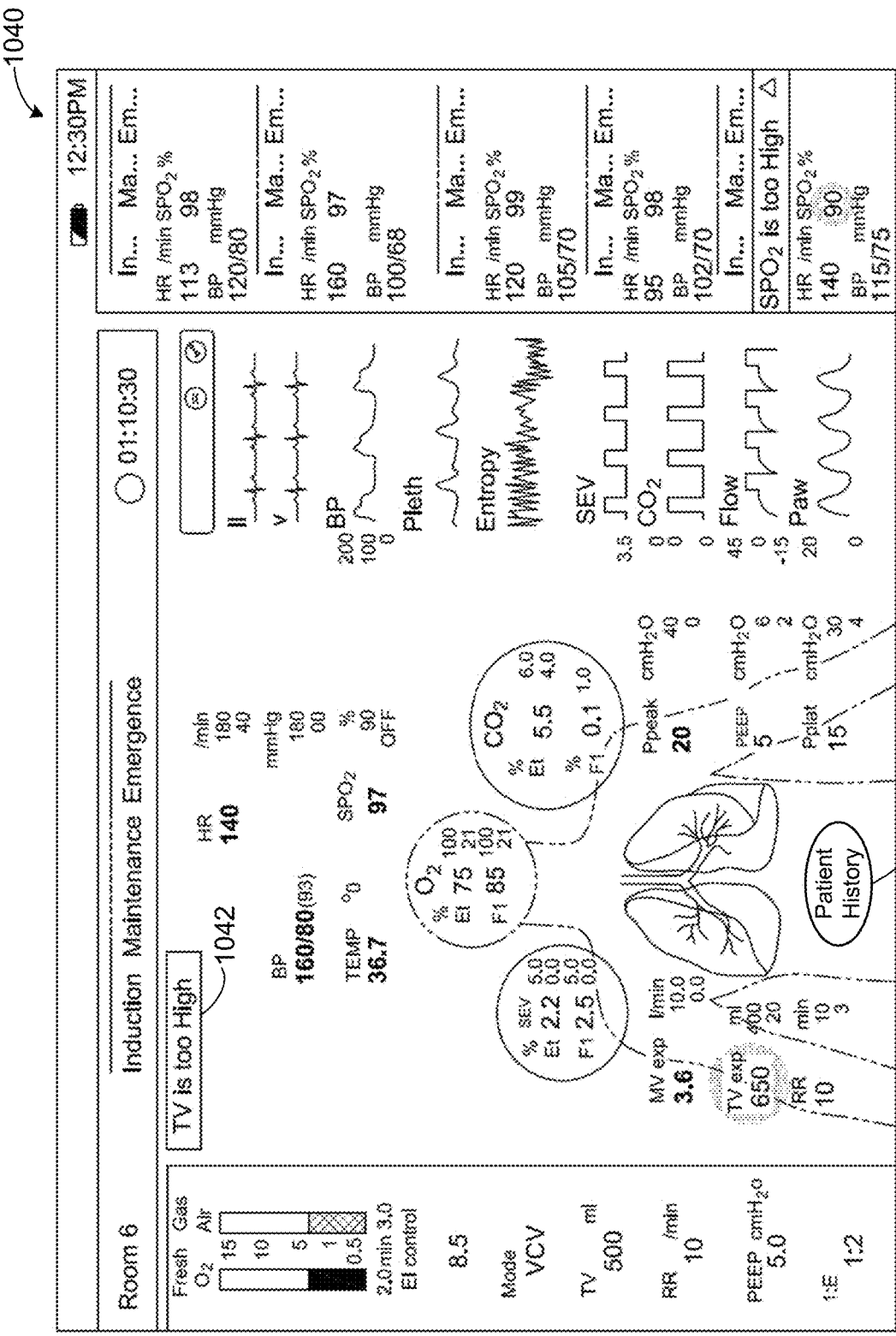

FIGS. 10A-10B illustrate a sequence of user interface screens corresponding to an example workflow for anomaly detection in patient data. As shown in the example of FIG. 10A, a multi-patient view interface 1000 provides representations 1010-1020 for a plurality of patients dynamically showing associated vitals and/or other physiological data (e.g., heart rate, blood pressure, oxygen saturation, etc.) including one or more warnings 1030, 1032, where applicable, for the respective patient. For example, the multi-patient view 1000 shows a real-time (or substantially real time given memory and/or processor latency, data transmission time, etc.) digest of physiological signals recorded over a period of time (e.g., the last five minutes, last ten minutes, last minute, etc.) for multiple patients.

Using the example interface 1000, a patient representation 1010-1020 can be selected to trigger an expanded single-patient view 1040, such as shown in the example of FIG. 10B, showing an expanded view of the representation 1020 for the selected patient. For example, a doctor can click one of the displayed patient representations 1010-1020 to see more real-time signals from that patient in the single patient view 1040 of the example of FIG. 10B. The signals can convey phases of a patient's care such as inductance, maintenance, and emergence phases of the patient's anesthesia, for example.

Whereas the multi-patient view 1000 may have a prioritized patient 1020, the single-patient view 1040 can include a prioritized event 1042. The example single-patient view 1040 can also include a button, icon, or other trigger 1045 to view a patient history for the patient displayed in the single view interface 1040. By clicking on the history data button 1045 in the single-patient view 1040, collected physiological signals for the patient over a given interval (e.g., in the past hour, the past 5 hours, the past 8 hours, etc.) is displayed.

As such, the example of FIGS. 10A-10B illustrates a new, interactive, dynamic user interface to allow correlation, processing, and viewing of a plurality of sets of patient data, focus on one set of patient data, concentration on a subset of such patients, in depth review of a particular patient, and deep dive into source 1D data and associated analysis. In certain examples, the series of interfaces 1000, 1040, can replace the prior interface upon opening, pop-up and/or otherwise overlay the prior interface upon opening, etc. The interface allows a patient and/or group of patients to be analyzed, diagnosed, treated, etc., and also facilitates transformation of gathered patient data into a verified data set for training, testing, etc., of AI model(s), for example.

Figure 11:
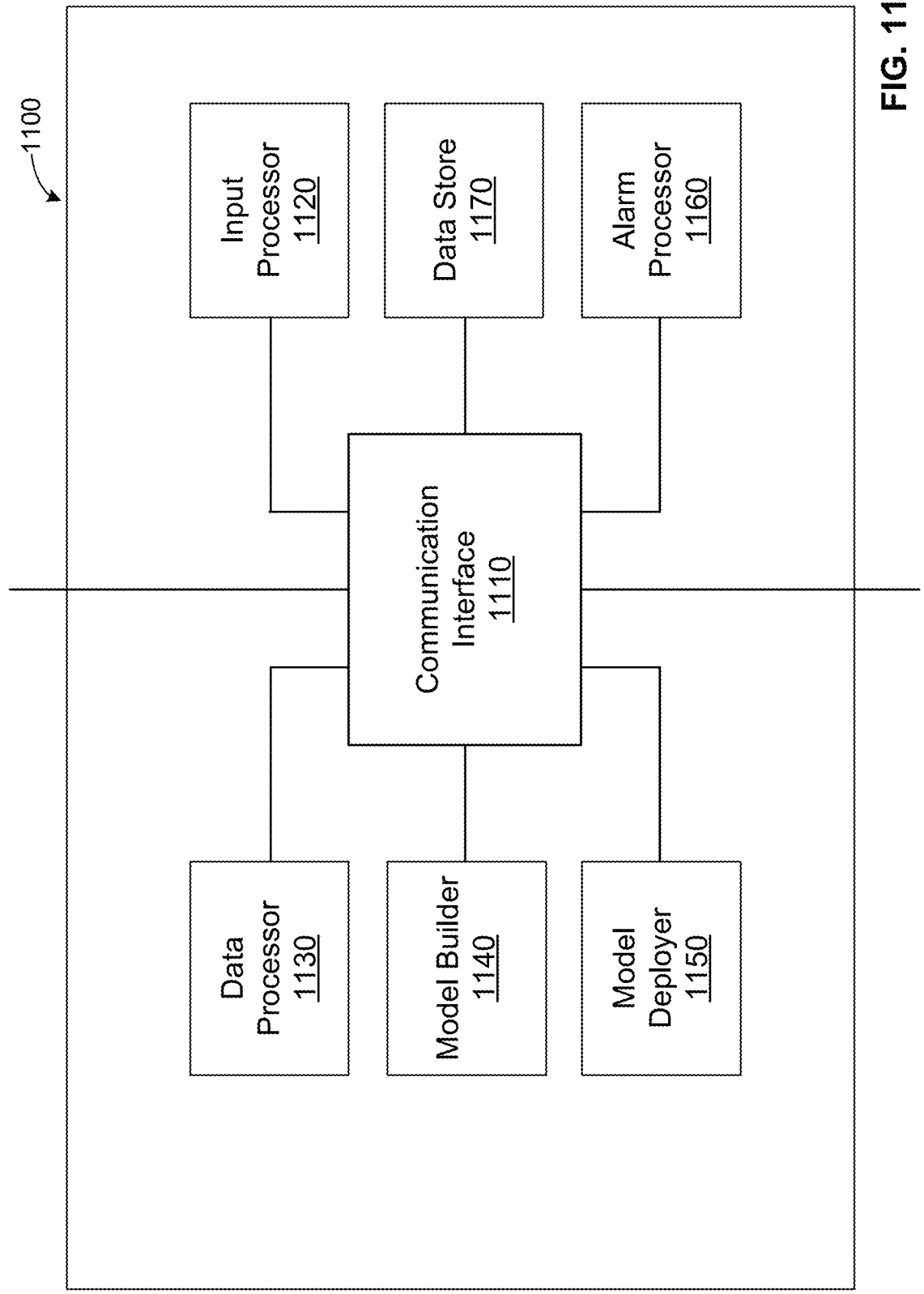
FIG. 11 illustrates an example time series data processing system.

FIG. 11 illustrates an example time series data processing system or apparatus 1100. The example system 1100 can be used to process 1D time series data from one or more patients to generate a detection, a classification, a prediction, and/or other output, for example. The example system 1100 includes a communication interface 1110, an input processor 1120, a data processor 1130, a model builder 1140, a model deployer 1150, an alarm processor 1160, and a data store 1170. The example system 1100 gathers from one or more medical devices, patient monitors, etc., to train an AI model, test an AI model, update an AI model, drive a deployed AI model to produce an output, etc.

The example communication interface 1110 is to send and receive data to/from one or more sources such as sensors, other monitoring devices, medical devices, other machines, information systems, imaging systems, archives, etc. The example input processor 1120 is to clean (e.g., remove outlier data, interpolate missing data, adjust data format, etc.), normalize (e.g., with respect to a normal value, reference value, standard value, threshold, etc.) and/or otherwise process incoming data (e.g., monitored patient physiological data, logged machine data, electronic medical record data, etc.) for further processing by the system 1100.

The example data processor 1130 processes the normalized and/or otherwise preprocessed data from the input processor 1120 to complete the normalization of data begun by the input processor, compare data provided by the input processor 1120 and/or directly from the communication interface 1110, prepare data for modeling (e.g., for training and/or testing a machine learning model, for visualization, for computer-aided diagnosis and/or detection, etc.), etc.

The example model builder 1140 builds a machine learning model (e.g., trains and tests a supervised machine learning neural network and/or other learning model, etc.) using data from the communication interface 1110, input processor 1120, and/or data processor 1130. For example, the model builder 1140 can leverage raw and/or normalized data, etc., to train and/or test a machine learning model (e.g., an RL model, hybrid RL model, CNN, DNN, etc.) to correlate output(s) with input(s) and test the accuracy of the model. The example model deployer 1150 can deploy an executable network model once the model builder 1140 is satisfied with the training and testing. The deployed model can be used to process data, correlate an output (e.g., a graphical representation, identification of an anomaly, identification of a trend, etc.) with input data, identify, classify, and/or predict an event, alarm, etc., from captured waveform data, etc.

The example alarm processor 1160 can be used to process an alarm detected, generated, classified, and/or predicted by the deployed model to trigger an alert (e.g., a visual displayed alert, an audible alert, an output to a log file and/or patient record/chart/worklist, etc.). As such, the example alarm processor 1160 can react to an output of the deployed model (e.g., the deployed hybrid RL model, etc.) to correct the alarm, notify regarding the alarm, further train regarding the alarm, and/or otherwise respond to the alarm, for example. The alarm processor 1160 can convey an instruction and/or other response to a display, other processor/system, etc., via the communication interface 1110, for example.

The example data store 1170 can be used to store physiological signal data, generated AI models, instructions for alarm processing and/or other computing tasks, etc. The data store 1170 can be used for temporary data storage or buffering (e.g., during training/testing, during processing by the deployed model, etc.) and/or for more permanent/longer lasting data storage, for example. The example data store 1170 can work with the alarm processor 1160, data processor 1130, input processor 1120, communication interface 1110, etc., to generate user interface displays, data manipulation, graphical representation manipulation, processing of data, access to external system(s)/process(es), data transfer, storage, reporting, etc., via the one or more interfaces such as shown in the examples of FIGS. 10A-10B, etc.

Figure 12:
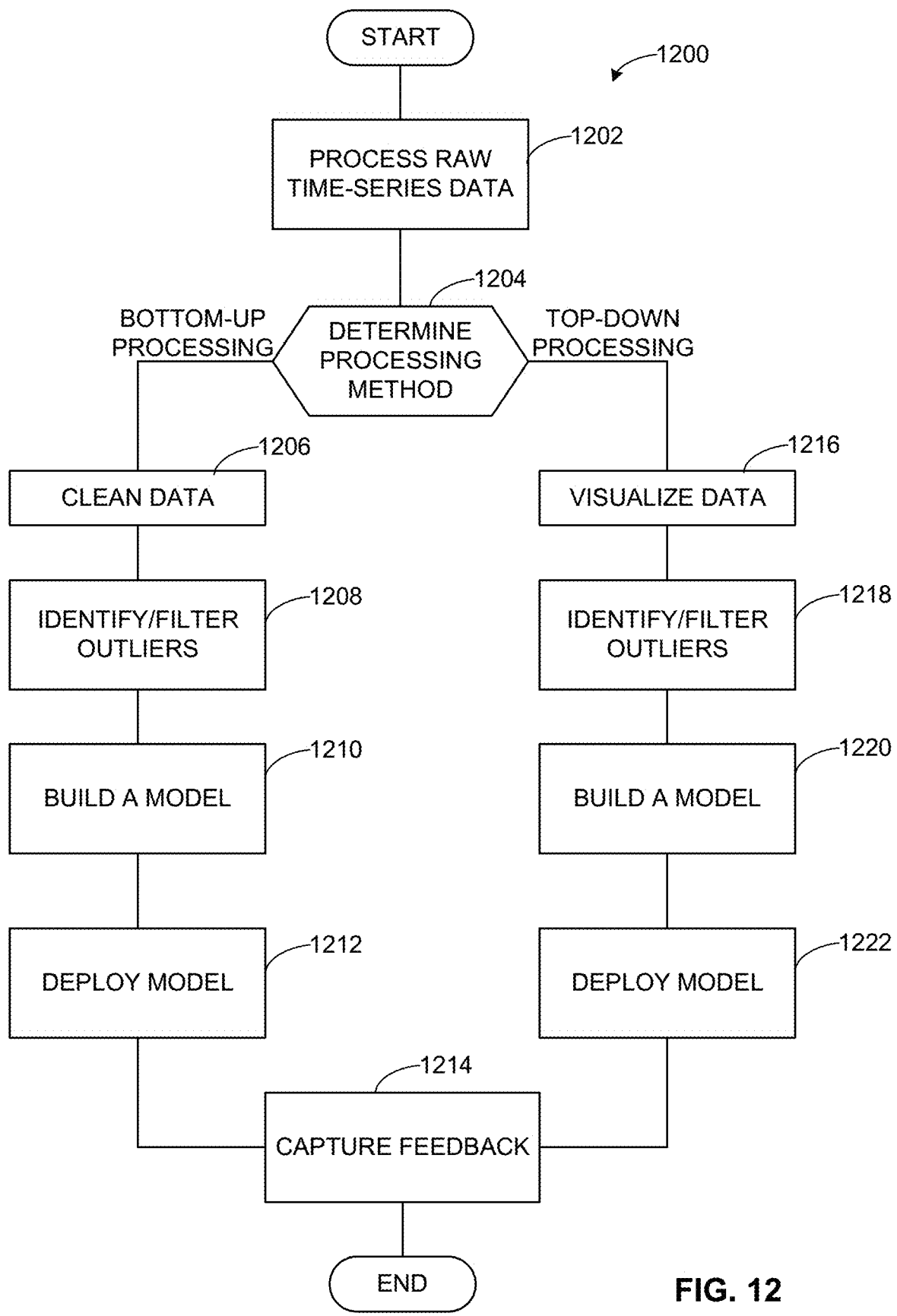
FIGS. 12-13 illustrate flow diagrams of example methods to process one-dimensional time series data using the example system(s) of FIGS. 1-9B.

FIG. 12 is a flow diagram of an example method 1200 to process 1D time series data. At block 1202, raw time series data is processed. For example, 1D waveform data from one or more sensor attached to and/or otherwise monitoring a patient, a medical device, other equipment, a healthcare environment, etc., can be processed by the example input processor 1120 to identify the data (e.g., type of data, format of data, source of data, etc.) and route the data appropriately.

At block 1204, a processing method to be applied to the data is determined. The processing method can be dynamically determined by the data processor 1130 based on the type of the data, source of the data, reason for exam, patient status, type of patient, associated healthcare professional, associated healthcare environment, etc. The processing method can be a bottom-up processing method or a top-down processing method, for example. When the processing method is to be a bottom-up processing method, at block 1206, the data is cleaned. For example, the data can be cleaned by the data processor 1130 to normalize the data with respect to other data and/or a reference/standard value. The data can be cleaned by the data processor 1130 to interpolate missing data in the time series, for example. The data can be cleaned by the data processor 1130 to adjust a format of the data, for example. At block 1208, outliers in the data are identified and filtered. For example, outlier data points that fall beyond a boundary, threshold, standard deviation, etc., are filtered (e.g., removed, separated, reduced, etc.) from the data being processed.

At block 1210, a model is built using the data. For example, the example model builder 1140 builds a machine learning model (e.g., trains and tests a supervised machine learning neural network and/or other learning model such as an unsupervised learning model, a deep learning model, a reinforcement learning model, a hybrid reinforcement learning model, etc.) using data from the communication interface 1110, input processor 1120, and/or data processor 1130. For example, the model builder 1140 can leverage normalized data, data transformed into the relative graphical visualization, etc., to train a machine learning model to correlate output(s) with input(s) and test the accuracy of the model.

At block 1212, the model is deployed. For example, the example model deployer 1150 can deploy an executable network model once the model builder 1140 is satisfied with the training and testing. The deployed model can be used to process data, correlate an output (e.g., a graphical representation, identification of an anomaly, identification of a trend, etc.) with input data, convert waveform data to a relative graphical representation, etc.

At block 1214, feedback is captured from use of the deployed model. For example, feedback can be captured from the deployed model itself, feedback can be captured from an application using the model, feedback can be captured from a human user, etc.

When the processing method is to be a top-down processing method, at block 1216, the data is visualized. For example, the example data processor 1130 can be used to process the data to transform the source waveform and/or other 1D time series data into graphical representations. At block 1218, outliers in the data are identified and filtered. For example, outlier data points that fall beyond a boundary, threshold, standard deviation, etc., are filtered (e.g., removed, separated, reduced, etc.) by the data processor 1130 from the data being processed. Filtering and/or other removal of outliers can be automatic by the data processor 1130 and/or can be triggered by interaction with the interface, data visualization, etc.

At block 1220, a model is built using the data. For example, the example model builder 1140 builds a model (e.g., trains and tests a supervised machine learning neural network and/or other learning model such as an unsupervised learning model, a deep learning model, a reinforcement learning model, a hybrid reinforcement learning model, etc.) using data. At block 1222, the model is deployed. For example, the example model deployer 1150 can deploy an executable model once the model builder 1140 is satisfied with the training and testing. The deployed model can be used to process data, correlate an output with input data, detect/classify/predict an alarm and/or other event, etc. As such, the model can be used to output prediction, classification, and/or detection results based on time-series data, for example.

At block 1214, feedback is captured from use of the deployed model. For example, feedback can be captured from the deployed model itself, feedback can be captured from an application using the model, feedback can be captured from a human user, etc.

Figure 13:
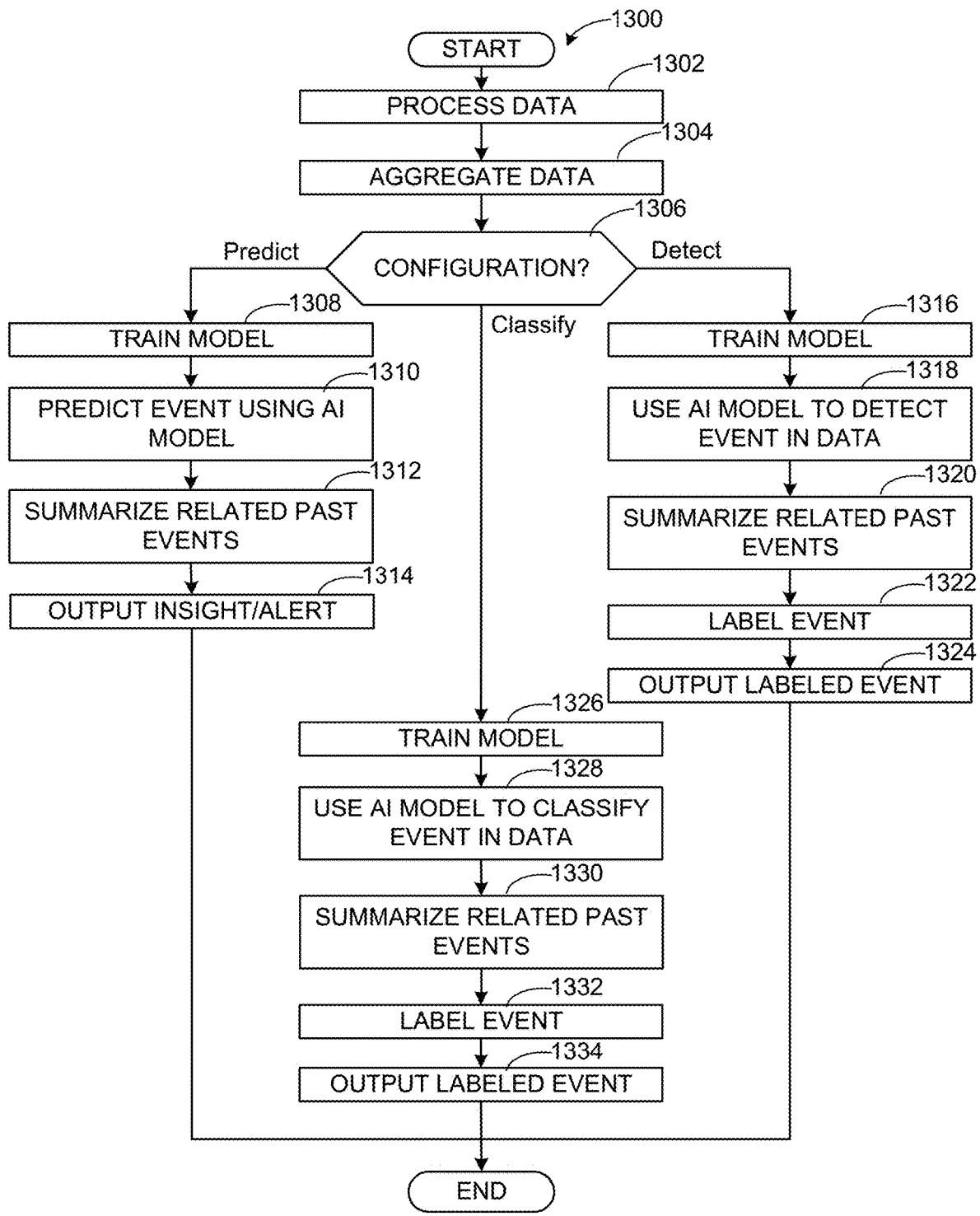

FIG. 13 is a flow diagram of an example method 1300 of processing 1D time series data using one or more AI models.

At block 1302, data is processed. For example, data captured during an ongoing procedure (e.g., in real time or substantially in real time given capture, transmission, processing, and/or storage latency) can be processed to convert or normalize the data into the data structure format for ease of analysis, comparison, etc. Data can also be retrieved from a data source offline (e.g., after and/or otherwise outside a healthcare procedure or equipment operation, etc.) and processed. At block 1304, the processed data is aggregated to form a data set for analysis (e.g., during a procedure, after/outside the procedure, etc.). At block 1306, a configuration or operating mode is analyzed to determine whether to a) predict a machine and/or patient event from a stream of data obtained during operation (e.g., in real time) or b) detect and classify a machine and/or patient event from a set of data obtained from a prior execution.

If predicting, then, at block 1308, one or more AI models are trained on aggregated time series data. For example, an RL model, a hybrid RL model, a deep learning model, a combination of hybrid RL+DL, etc., are trained on a set of aggregated time series data such as patient physiological data, machine data, etc. Patient physiological data includes one or more of vitals, heart rate, heart rhythm, blood pressure (systolic and diastolic), etc. Machine data includes one or more of tidal volume, patient-controlled anesthesia (PCA) (e.g., an injection, etc.), PCA lockout (minimum), PCA medication, PCA total dose, etc. The gathered/captured data can be normalized and/or standardized to a data structure format for ease of analysis, comparison, etc. Once trained, the AI model(s) are deployed for use.

At block 1310, the one or more trained AI models are used to predict an events in the stream/set of data. For example, one or more trained AI models such as a hybrid RL model, GNN model, transformer network model, LSTM model, GCN model, other DL model, etc., are used to process the data and predict a future event based on the data. For example, based on analysis of the data (e.g., its content, its patterns, its boundaries, etc.) by the model(s), one or more events are predicted with respect to the patient being monitored, one or more medical machines/devices applied to the patient and monitored, etc. Alarm and/or non-alarm events can be predicted based on the captured 1D data stream passing through the AI model(s) (e.g., a hybrid RL model with a DL model, etc.). For example, flow of gas (e.g., anesthesia, etc.), emergence of patient, end of case, stroke, clinical event, etc., can be predicted.

At block 1312, past events related to the predicted event are summarized. For example, historical data regarding similar or related events can be processed in comparison and/or other relation to the predicted event. The past events can be used to characterize the predicted event as an alarm or non-alarm event, for example. The past events can be used to determine an action in response to the predicted event, for example.

At block 1314, an insight and/or alert is generated and output based on the predicted event and the summary of past related events. For example, a comparison and/or other analysis of the predicted event and the past events can generate an insight into a type of the predicted event, a likely cause of the predicted event, a likely result of the predicted event, a proposed remedy for the predicted event, a logged alert of the predicted event, an audiovisual alert of the predicted event, a trigger resulting from the predicted event, etc.

If detecting, then, at block 1316, one or more AI models are trained on aggregated time series data. For example, an RL model, a hybrid RL model, a deep learning model, a combination of hybrid RL+DL, etc., are trained on a set of aggregated time series data such as patient physiological data, machine data, etc. Patient physiological data includes one or more of vitals, heart rate, heart rhythm, blood pressure (systolic and diastolic), etc. Machine data includes one or more of tidal volume, patient-controlled anesthesia (PCA) (e.g., an injection, etc.), PCA lockout (minimum), PCA medication, PCA total dose, etc. The gathered/captured data can be normalized and/or standardized to a data structure format for ease of analysis, comparison, etc. Once trained, the AI model(s) are deployed for use.

At block 1318, the one or more trained AI models are used to detect an event in the stream/set of data. For example, one or more trained AI models such as a hybrid RL model, GNN model, transformer network model, LSTM model, GCN model, other DL model, etc., are used to process the data and identify or detect an event in the data. For example, based on analysis of the data (e.g., its content, its patterns, its boundaries, etc.) by the model(s), one or more events are detected with respect to the patient being monitored, one or more medical machines/devices applied to the patient and monitored, etc.

Alarm and/or non-alarm events can be detected based on the captured 1D data stream passing through the AI model(s) (e.g., a hybrid RL model with a DL model, etc.), which the AI model(s) serving as ground truth against which to identify the event(s). For example, flow of gas (e.g., anesthesia, etc.), emergence of patient, end of case, stroke, clinical event, etc., can be detected using the model(s).

At block 1320, past events related to the detected event are summarized. For example, historical data regarding similar or related events can be processed in comparison and/or other relation to the detected event. The past events can be used to characterize the detected event as an alarm or non-alarm event, for example. The past events can be used to determine an action in response to the detected event, for example.

At block 1322, the detected event is labeled. For example, the detected event can be labeled as an alarm event, a non-alarm event, more specifically as a gas start event, a gas stop event, a stroke event, an emergence event, a clinical event, a machine event, a patient event, etc.

At block 1324, the labeled event is output. For example, the labeled event can be written to an electronic medical record, used to trigger an appointment in a clinical scheduling system, used to trigger a lab request, used to trigger an exam request, used to prioritize image and/or other exam data in a radiology reading, displayed for user view and interaction, etc.

If classifying, then, at block 1326, one or more AI models are trained on aggregated time series data. For example, an RL model, a hybrid RL model, a deep learning model, a combination of hybrid RL+DL, etc., are trained on a set of aggregated time series data such as patient physiological data, machine data, etc. Patient physiological data includes one or more of vitals, heart rate, heart rhythm, blood pressure (systolic and diastolic), etc. Machine data includes one or more of tidal volume, patient-controlled anesthesia (PCA) (e.g., an injection, etc.), PCA lockout (minimum), PCA medication, PCA total dose, etc. The gathered/captured data can be normalized and/or standardized to a data structure format for ease of analysis, comparison, etc. Once trained, the AI model(s) are deployed for use.

At block 1328, an event is classified. For example, one or more trained AI models such as a hybrid RL model, GNN model, transformer network model, LSTM model, GCN model, other DL model, etc., are used to process and classify an event in the data. The event can be classified as an alarm event, a non-alarm event, an event of a certain type, etc.

For example, based on analysis of the data (e.g., its content, its patterns, its boundaries, etc.) by the model(s), one or more events are classified in a stream/set of data with respect to the patient being monitored, one or more medical machines/devices applied to the patient and monitored, etc. Alarm and/or non-alarm events can be classified based on the captured 1D data stream passing through the AI model(s) (e.g., a hybrid RL model with a DL model, etc.), which the AI model(s) serving as ground truth against which to identify the event(s). For example, flow of gas (e.g., anesthesia, etc.), emergence of patient, end of case, stroke, clinical event, etc., can be detected using the model(s).

At block 1330, past events related to the classified event are summarized. For example, historical data regarding similar or related events can be processed in comparison and/or other relation to the detected event. The past events can be used to characterize the detected event as an alarm or non-alarm event, for example. The past events can be used to determine an action in response to the detected event, for example.

At block 1332, the classified event is labeled. For example, the classified event can be labeled as an alarm event, a non-alarm event, more specifically as a gas start event, a gas stop event, a stroke event, an emergence event, a clinical event, a machine event, a patient event, etc.

At block 1334, the labeled event is output. For example, the labeled event can be written to an electronic medical record, used to trigger an appointment in a clinical scheduling system, used to trigger a lab request, used to trigger an exam request, used to prioritize image and/or other exam data in a radiology reading, displayed for user view and interaction, etc.

In certain examples, the configuration at block 1306 can repeat such that an event can be detected and then classified. A detected and/or classified event can be used to predict a next event, for example.

Thus, an event can be predicted during a medical procedure, for example. Detection and classification of an event can occur after the procedure, for example. A predicted and/or detected event can be highlighted to a user, used to trigger another device/system, used to trigger corrective/responsive action, etc.

While example implementations are disclosed and described herein, processes and/or devices disclosed and described herein can be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Flowcharts representative of example machine readable instructions for implementing components are disclosed and described herein. In the examples, the machine readable instructions include a program for execution by a processor. The program may be embodied in machine readable instructions stored on a tangible computer readable storage medium such as a CD-ROM, a floppy disk, a hard drive, a digital versatile disk (DVD), a Blu-ray disk, or a memory associated with the processor, but the entire program and/or parts thereof could alternatively be executed by a device other than the processor and/or embodied in firmware or dedicated hardware. Further, although the example program is described with reference to flowchart(s), many other methods of implementing the components disclosed and described herein may alternatively be used. For example, the order of execution of the blocks may be changed, and/or some of the blocks described may be changed, eliminated, or combined. Although the flowchart(s) depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example process(es) can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process(es) can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

Figure 14:
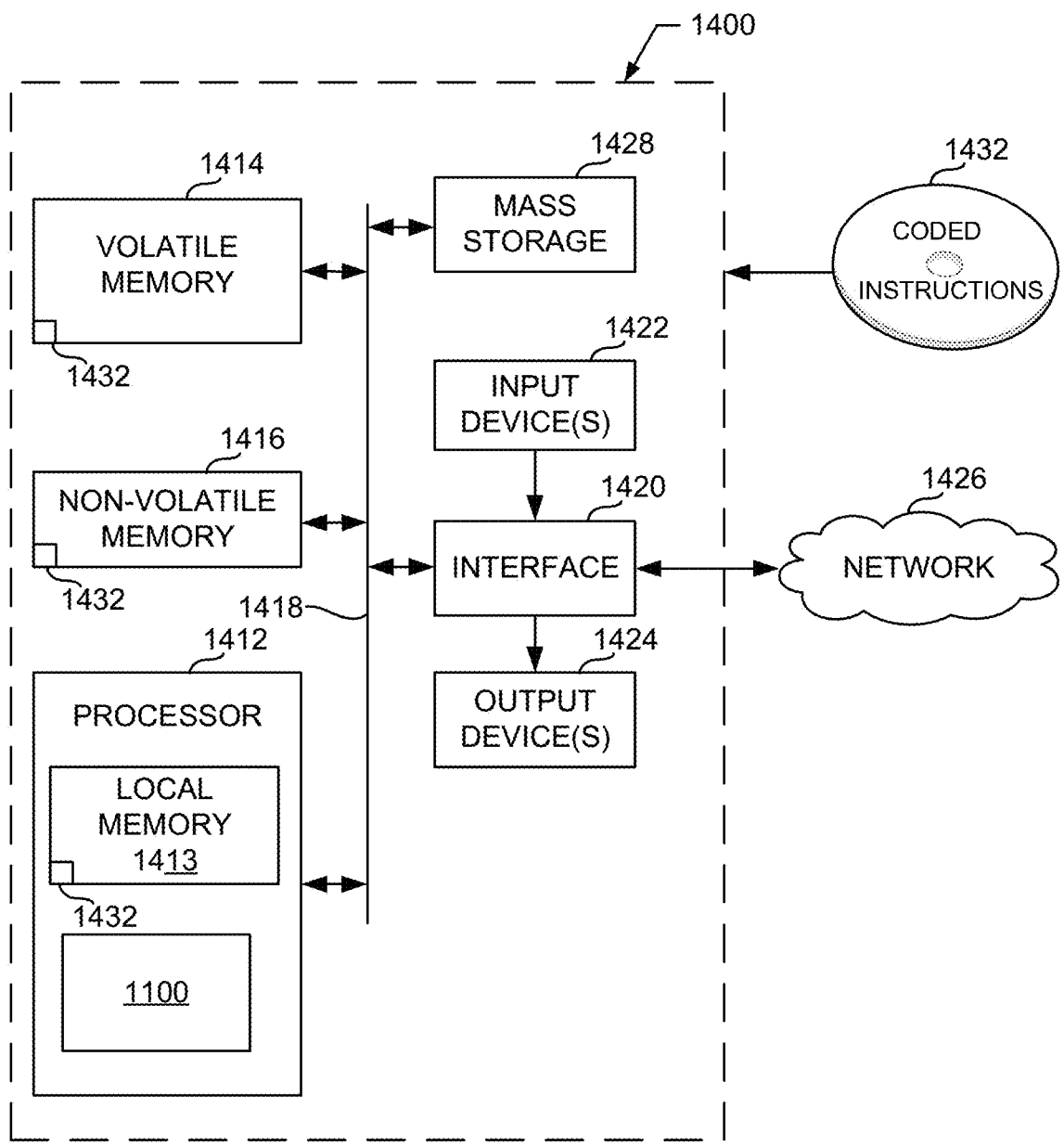
FIG. 14 is a block diagram of an example processor platform capable of executing instructions to implement the example systems and methods disclosed and described herein.

FIG. 14 is a block diagram of an example processor platform 1400 structured to execute the instructions of FIGS. 12-13 to implement, for example the example apparatus 1100 of FIG. 11. The processor platform 1400 can be, for example, a server, a personal computer, a workstation, a self-learning machine (e.g., a neural network), a mobile device (e.g., a cell phone, a smart phone, a tablet such as an iPad'), a personal digital assistant (PDA), an Internet appliance, a gaming console, a personal video recorder, a set top box, a headset or other wearable device, or any other type of computing device.

The processor platform 1400 of the illustrated example includes a processor 1412. The processor 1412 of the illustrated example is hardware. For example, the processor 1412 can be implemented by one or more integrated circuits, logic circuits, microprocessors, GPUs, DSPs, or controllers from any desired family or manufacturer. The hardware processor may be a semiconductor based (e.g., silicon based) device. In this example, the processor 1412 implements the example apparatus 1100 but can also be used to implement other systems disclosed herein such as systems 100, 200, 300, 400, 410, 420, 430, 440, 450, 700, 800, 900, etc.

The processor 1412 of the illustrated example includes a local memory 1413 (e.g., a cache). The processor 1412 of the illustrated example is in communication with a main memory including a volatile memory 1414 and a non-volatile memory 1416 via a bus 1418. The volatile memory 1414 may be implemented by SDRAM, DRAM, RDRAM®, and/or any other type of random access memory device. The non-volatile memory 1416 may be implemented by flash memory and/or any other desired type of memory device. Access to the main memory 1414, 1416 is controlled by a memory controller.

The processor platform 1400 of the illustrated example also includes an interface circuit 1420. The interface circuit 1420 may be implemented by any type of interface standard, such as an Ethernet interface, a USB, a Bluetooth® interface, an NFC interface, and/or a PCI express interface.

In the illustrated example, one or more input devices 1422 are connected to the interface circuit 1420. The input device(s) 1422 permit(s) a user to enter data and/or commands into the processor 1412. The input device(s) can be implemented by, for example, an audio sensor, a microphone, a camera (still or video), a keyboard, a button, a mouse, a touchscreen, a track-pad, a trackball, isopoint, and/or a voice recognition system.

One or more output devices 1424 are also connected to the interface circuit 1420 of the illustrated example. The output devices 1424 can be implemented, for example, by display devices (e.g., an LED, an OLED, an LCD, a CRT display, an IPS display, a touchscreen, etc.), a tactile output device, a printer, and/or speaker. The interface circuit 1420 of the illustrated example, thus, typically includes a graphics driver card, a graphics driver chip, and/or a graphics driver processor.

The interface circuit 1420 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1426. The communication can be via, for example, an Ethernet connection, a DSL connection, a telephone line connection, a coaxial cable system, a satellite system, a line-of-site wireless system, a cellular telephone system, etc.

The processor platform 1400 of the illustrated example also includes one or more mass storage devices 1428 for storing software and/or data. Examples of such mass storage devices 1428 include floppy disk drives, hard drive disks, compact disk drives, Blu-ray disk drives, RAID systems, and DVD drives.

The machine executable instructions 1432 of FIGS. 12-13 may be stored in the mass storage device 1428, in the volatile memory 1414, in the non-volatile memory 1416, and/or on a removable non-transitory computer readable storage medium such as a CD or DVD.

From the foregoing, it will be appreciated that example methods, apparatus and articles of manufacture have been disclosed that improve healthcare AI network construction, testing, deployment, etc. The disclosed apparatus, systems, methods, and articles of manufacture improve the efficiency and effectiveness of the processor system, memory, and other associated circuitry by leverage artificial intelligence models, transformations of waveform and/or other time-series data into prediction, detection, and or classification of machine/patient events in healthcare data, etc. The disclosed methods, apparatus and articles of manufacture are accordingly directed to one or more improvement(s) in the functioning of a computer and/or other processor and its associated interface. The apparatus, methods, systems, instructions, and media disclosed herein are not implementable in a human mind and are not able to be manually implemented by a human user.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A time series event data processing apparatus comprising:
   memory storing instructions and one-dimensional time series healthcare-related data from at least one of a patient or a medical machine; and
   at least one processor to:
   facilitate selection of one or more artificial intelligence models from a plurality of artificial intelligence models trained on aggregated one-dimensional time series data and including at least: a) a first model to predict occurrence of a future medical machine event, b) a second model to detect an occurring medical machine event, and c) a third model to classify a medical machine event that has already occurred; and execute the selected one or more artificial intelligence models to process one-dimensional time series healthcare-related data to generate a determination, wherein:

when the selected one or more artificial intelligence models includes the first model executed to predict the future medical machine event, i) the determination includes the predicted future medical machine event and ii) the at least one processor is to output, based on the determination, an alert related to the predicted future medical machine event to trigger a next action involving at least one of the medical machine or another device;

when the selected one or more artificial intelligence models includes the second model executed to detect the occurring medical machine event, the determination includes the detected occurring medical machine event and ii) the at least one processor is to label, based on the determination, the detected occurring medical machine event and output the labeled event to trigger the next action involving at least one of the medical machine or another device; and when the selected one or more artificial intelligence models includes the third model executed to classify the medical machine event that has already occurred, the determination includes a classification of the medical machine event that has already occurred and ii) the at least one processor is to label, based on the determination, the medical machine event that has already occurred and output the labeled event to trigger the next action involving at least one of the medical machine or another device, and wherein the plurality of artificial intelligence models includes at least one of a reinforcement learning model, a hybrid reinforcement learning model, a graph neural network model, or a transformer network model.

2. The apparatus of claim 1, wherein the selected one or more artificial intelligence models includes the hybrid reinforcement learning model including a model-based processor, a model-free processor, and a configurable parameter to select between the model-based processor and the model-free processor based on a state of the first set of one-dimensional time series healthcare-related data.

3. The apparatus of claim 2, wherein the selected one or more artificial intelligence models includes the hybrid reinforcement learning model with a deep learning network model.

4. The apparatus of claim 1, wherein the one-dimensional time series healthcare-related data includes at least one of patient physiological waveform signal data or medical machine operating signal data.

5. The apparatus of claim 1, wherein the at least one processor is to aggregate the one-dimensional time series healthcare-related data using at least one of K-means, a Gaussian mixture model, or a density-based spatial clustering of applications with noise.

6. The apparatus of claim 1, further including a user interface display to display the at least one of the alert or the labeled event.

7. The apparatus of claim 1, wherein the at least one processor is to execute the selected one or more artificial intelligence models to at least one of a) predict a future patient event, b) detect a patient event, or c) classify the patient event using the one-dimensional time series healthcare-related data.

8. At least one tangible computer-readable storage medium comprising instructions that, when executed, cause at least one processor to at least:

facilitate selection of one or more artificial intelligence models from a plurality of artificial intelligence models trained on aggregated one-dimensional time series data and including at least: a) a first model to predict occurrence of a future medical machine event, b) a second model to detect an occurring medical machine event, and c) a third model to classify a medical machine event that has already occurred; and execute the selected one or more artificial intelligence models to process one-dimensional time series healthcare-related data to generate a determination, wherein:

when the selected one or more artificial intelligence models includes the first model executed to predict the future medical machine event, i) the determination includes the predicted future medical machine event and ii) the at least one processor is to output, based on the determination, an alert related to the predicted future medical machine event to trigger a next action involving at least one of the medical machine or another device;

when the selected one or more artificial intelligence models includes the second model executed to detect the occurring medical machine event, i) the determination includes the detected occurring medical machine event and ii) the at least one processor is to label, based on the determination, the detected occurring medical machine event and output the labeled event to trigger the next action involving at least one of the medical machine or another device; and when the selected one or more artificial intelligence models includes the third model executed to classify the medical machine event that has already occurred, i) the determination includes a classification of the medical machine event that has already occurred and ii) the at least one processor is to label, based on the determination, the medical machine event that has already occurred and output the labeled event to trigger the next action involving at least one of the medical machine or another device, and wherein the one or more artificial intelligence models includes at least one of a reinforcement learning model, a hybrid reinforcement learning model, a graph neural network model, or a transformer network model.

9. The at least one tangible computer-readable storage medium of claim 8, wherein the selected one or more artificial intelligence models includes the hybrid reinforcement learning model including a model-based processor, a model-free processor, and a configurable parameter to select between the model-based processor and the model-free processor based on a state of the one-dimensional time series healthcare-related data.

10. The at least one tangible computer-readable storage medium of claim 9, wherein the selected one or more artificial intelligence models includes the hybrid reinforcement learning model with a deep learning network model.

11. The at least one tangible computer-readable storage medium of claim 8, wherein the instructions, when executed, cause the at least one processor to convert the one-dimensional time series healthcare-related data to a first data structure format.

12. The at least one tangible computer-readable storage medium of claim 8, wherein the one-dimensional time series healthcare-related data includes at least one of patient physiological waveform signal data or medical machine operating signal data.

13. The at least one tangible computer-readable storage medium of claim 8, wherein the instructions, when executed, cause the at least one processor to aggregate the one-dimensional time series healthcare-related data using at least one of K-means, a Gaussian mixture model, or a density-based spatial clustering of applications with noise.

14. The at least one tangible computer-readable storage medium of claim 8, wherein the instructions, when executed, cause the at least one processor to execute the selected one or more artificial intelligence models to at least one of a) predict a future patient event, b) detect a patient event, or c) classify the patient event using the one-dimensional time series healthcare-related data.

15. A computer-implemented method for medical machine time-series event data processing, the method comprising:

facilitating selection of one or more artificial intelligence models from a plurality of artificial intelligence models trained on aggregated one-dimensional time series data and including at least: a) a first model to predict occurrence of a future medical machine event, b) a second model to detect an occurring medical machine event, and c) a third model to classify a medical machine event that has already occurred; and executing the selected one or more artificial intelligence models to process one-dimensional time series healthcare-related data to generate a determination, wherein:

when the selected one or more artificial intelligence models includes the first model executed to predict occurrence of the future medical machine event, outputting, based on the determination, an alert related to the predicted future medical machine event to trigger a next action involving at least one of the medical machine or another device, the determination including the predicted occurrence of the future medical machine event;

when the selected one or more artificial intelligence models includes the second model executed to detect the occurring medical machine event, labeling, based on the determination, the detected occurring medical machine event and outputting the labeled event to trigger the next action involving at least one of the medical machine or another device, the determination including the detected occurring medical machine event; and when the selected one or more artificial intelligence models includes the third model executed to classify the medical machine event that has already occurred, labeling, based on the determination, the medical machine event that has already occurred and output the labeled event to trigger the next action involving at least one of the medical machine or another device, the determination including the detected medical machine event that has already occurred, wherein the plurality of one or more artificial intelligence models includes a reinforcement learning model, a hybrid reinforcement learning model, a graph neural network model, or a transformer network model.

16. The method of claim 15, wherein the one-dimensional time series healthcare-related data includes patient physiological signals and medical machine waveform data, and wherein the selected one or more artificial intelligence models includes the hybrid reinforcement learning model including a model-based processor, a model-free processor, and a configurable parameter to select between the model-based processor and the model-free processor based on a state of the one-dimensional time series healthcare-related data.

17. The method of claim 16, wherein the selected one or more artificial intelligence models includes the hybrid reinforcement learning model with a deep learning network model.

18. The method of claim 15, further including aggregating the one-dimensional time series healthcare-related data using at least one of K-means, a Gaussian mixture model, or a density-based spatial clustering of applications with noise.

19. The method of claim 15, wherein the one-dimensional time series healthcare-related data includes at least one of patient physiological waveform signal data or medical machine operating signal data.

20. The method of claim 15, further including executing the selected one or more artificial intelligence models to at least one of a) predict a future patient event, b) detect a patient event, or c) classify the patient event using the one-dimensional time series healthcare-related data.

* * * * *